United States Patent
Sokolovskii et al.

(10) Patent No.: US 10,722,869 B2
(45) Date of Patent: Jul. 28, 2020

(54) POROUS SHAPED METAL-CARBON PRODUCTS

(71) Applicant: Archer-Daniels-Midland Company, Decatur, IL (US)

(72) Inventors: Valery Sokolovskii, Santa Clara, CA (US); Alfred Hagemeyer, Sunnyvale, CA (US); James A. W. Shoemaker, Gilroy, CA (US); Elif Ispir Gürbüz, San Francisco, CA (US); Guang Zhu, Union City, CA (US); Eric L. Dias, Belmont, CA (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 16/662,914

(22) Filed: Oct. 24, 2019

(65) Prior Publication Data
US 2020/0055029 A1    Feb. 20, 2020

Related U.S. Application Data

(62) Division of application No. 15/132,048, filed on Apr. 18, 2016, now Pat. No. 10,464,048.

(Continued)

(51) Int. Cl.
| | |
|---|---|
| *B01J 23/755* | (2006.01) |
| *B01J 35/02* | (2006.01) |
| *B01J 23/42* | (2006.01) |
| *B01J 23/30* | (2006.01) |
| *C07C 51/31* | (2006.01) |
| *B01J 27/22* | (2006.01) |
| *B01J 35/10* | (2006.01) |
| *C09C 1/48* | (2006.01) |
| *C04B 35/532* | (2006.01) |
| *C07C 51/377* | (2006.01) |
| *C01B 32/354* | (2017.01) |
| *C04B 35/117* | (2006.01) |
| *C04B 35/636* | (2006.01) |
| *C04B 35/111* | (2006.01) |
| *B01J 21/18* | (2006.01) |
| *B01J 23/652* | (2006.01) |
| *B01J 23/68* | (2006.01) |
| *B01J 35/00* | (2006.01) |

(Continued)

(52) U.S. Cl.
CPC ............ *B01J 23/755* (2013.01); *B01J 21/18* (2013.01); *B01J 23/30* (2013.01); *B01J 23/42* (2013.01); *B01J 23/6527* (2013.01); *B01J 23/687* (2013.01); *B01J 27/22* (2013.01); *B01J 35/0006* (2013.01); *B01J 35/023* (2013.01); *B01J 35/026* (2013.01); *B01J 35/04* (2013.01); *B01J 35/1004* (2013.01); *B01J 35/1033* (2013.01); *B01J 35/1038* (2013.01); *B01J 35/1042* (2013.01); *B01J 35/1061* (2013.01); *B01J 35/1066* (2013.01); *B01J 37/0018* (2013.01); *B01J 37/04* (2013.01); *B01J 37/084* (2013.01); *B01J 37/18* (2013.01); *C01B 32/382* (2017.08); *C04B 35/111* (2013.01); *C04B 35/117* (2013.01); *C04B 35/532* (2013.01); *C04B 35/636* (2013.01); *C04B 35/6365* (2013.01); *C07C 29/60* (2013.01); *C07C 51/313* (2013.01); *C07C 51/377* (2013.01); *C07C 209/16* (2013.01); *C07D 307/20* (2013.01); *C09C 1/48* (2013.01); *B01J 2523/00* (2013.01); *C01P 2004/60* (2013.01); *C01P 2006/12* (2013.01); *C01P 2006/16* (2013.01); *C04B 2235/3258* (2013.01); *C04B 2235/3279* (2013.01); *C04B 2235/40* (2013.01); *C04B 2235/404* (2013.01); *C04B 2235/405* (2013.01); *C04B 2235/407* (2013.01); *C04B 2235/408* (2013.01); *C04B 2235/424* (2013.01); *C04B 2235/442* (2013.01); *C04B 2235/5409* (2013.01); *C04B 2235/6021* (2013.01); *C04B 2235/658* (2013.01); *C04B 2235/6562* (2013.01); *C04B 2235/6567* (2013.01); *C04B 2235/6582* (2013.01); *C04B 2235/6586* (2013.01); *C04B 2235/664* (2013.01)

(58) Field of Classification Search
None
See application file for complete search history.

(56) References Cited

U.S. PATENT DOCUMENTS

| 2,382,586 A | 8/1945 | Solomon et al. |
| 2,719,779 A | 1/1950 | Bray et al. |

(Continued)

FOREIGN PATENT DOCUMENTS

| CN | 101102904 A | 1/2008 |
| CN | 102701183 A | 10/2012 |

(Continued)

OTHER PUBLICATIONS

Asbury Carbons, Graphite and Carbon Powders for...Grease and Lubricant Manufactures, Asbury Graphite Mills, Inc. 405 Old Main Street, Asbury, NJ 08802, www.asbury.com, Jun. 2013, 1 page.

(Continued)

*Primary Examiner* — Guinever S Gregorio
(74) *Attorney, Agent, or Firm* — Stinson LLP

(57) ABSTRACT

The present invention provides a porous metal-containing carbon-based material that is stable at high temperatures under aqueous conditions. The porous metal-containing carbon-based materials are particularly useful in catalytic applications. Also provided, are methods for making and using porous shaped metal-carbon products prepared from these materials.

20 Claims, No Drawings

Related U.S. Application Data

(60) Provisional application No. 62/247,727, filed on Oct. 28, 2015.

(51) Int. Cl.

| | | |
|---|---|---|
| *B01J 35/04* | (2006.01) | |
| *B01J 37/00* | (2006.01) | |
| *B01J 37/04* | (2006.01) | |
| *B01J 37/08* | (2006.01) | |
| *B01J 37/18* | (2006.01) | |
| *C07C 29/60* | (2006.01) | |
| *C07C 209/16* | (2006.01) | |
| *C07D 307/20* | (2006.01) | |

(56) References Cited

U.S. PATENT DOCUMENTS

| | | |
|---|---|---|
| 2,754,330 A | 7/1956 | Schreyer |
| 2,850,403 A | 9/1958 | Day et al. |
| 3,127,356 A | 3/1964 | Hamilton et al. |
| 3,171,720 A | 3/1965 | Shea, Jr. et al. |
| 3,268,588 A | 8/1966 | Horlenko et al. |
| 3,270,059 A | 8/1966 | Winderl et al. |
| 3,329,626 A | 7/1967 | Teter et al. |
| 3,413,152 A | 11/1968 | Folkins et al. |
| 3,859,421 A | 1/1975 | Hucke |
| 3,978,000 A | 8/1976 | Schmitt, Jr. et al. |
| 4,029,600 A | 6/1977 | Schmitt, Jr. et al. |
| 4,031,137 A | 6/1977 | Schmitt, Jr. et al. |
| 4,035,260 A | 7/1977 | Schmitt, Jr. et al. |
| 4,399,052 A | 8/1983 | Sugino |
| 4,591,578 A | 5/1986 | Foley et al. |
| 4,777,303 A | 10/1988 | Kitson et al. |
| 4,804,791 A | 2/1989 | Kitson et al. |
| 5,015,773 A | 5/1991 | Dobson |
| 5,149,680 A | 9/1992 | Kitson et al. |
| 5,472,648 A | 12/1995 | Alisch et al. |
| 5,478,952 A | 12/1995 | Schwartz |
| 5,726,118 A | 3/1998 | Ivey et al. |
| 5,736,481 A | 4/1998 | Miller et al. |
| 5,846,639 A | 12/1998 | Robinson et al. |
| 5,872,177 A | 2/1999 | Whitehouse |
| 5,916,838 A | 6/1999 | Wulff-Döring et al. |
| 5,958,825 A | 9/1999 | Wulff-Döring et al. |
| 6,180,738 B1 | 1/2001 | Wang et al. |
| 6,207,264 B1 | 3/2001 | Robinson et al. |
| 6,258,864 B1 | 7/2001 | Dalton et al. |
| 6,337,302 B1 | 1/2002 | Teng et al. |
| 6,471,763 B1 | 10/2002 | Karl |
| 6,500,401 B2 | 12/2002 | Reznek et al. |
| 6,573,212 B2 | 6/2003 | McCrae et al. |
| 6,682,667 B1 | 1/2004 | Matviya |
| 6,787,029 B2 | 9/2004 | Gaudet et al. |
| 6,989,348 B2 | 1/2006 | Eijsbouts |
| 6,992,037 B2 | 1/2006 | Chen et al. |
| 7,008,534 B2 | 3/2006 | Gaudet et al. |
| 7,195,713 B2 | 3/2007 | Gaudet et al. |
| 7,358,004 B2 | 4/2008 | Igarashi et al. |
| 7,651,772 B2 | 1/2010 | Lee |
| 7,754,922 B2 | 7/2010 | Kubanek et al. |
| 7,906,453 B2 | 3/2011 | Ezenyilimba et al. |
| 7,922,805 B2 | 4/2011 | Kowalski et al. |
| 7,951,297 B2 | 5/2011 | Gaudet et al. |
| 8,501,989 B2 | 8/2013 | Boussie et al. |
| 8,585,816 B2 | 11/2013 | Shim et al. |
| 8,657,483 B2 | 2/2014 | Nebergall et al. |
| 8,669,393 B2 | 3/2014 | Boussie et al. |
| 8,669,397 B2 | 3/2014 | Boussie et al. |
| 8,728,223 B2 | 5/2014 | Shim et al. |
| 8,759,250 B2 | 6/2014 | Robinson et al. |
| 8,759,253 B2 | 6/2014 | De Leede et al. |
| 8,785,683 B2 | 7/2014 | Boussie et al. |
| 9,682,368 B2 | 6/2017 | Dias et al. |
| 2002/0077504 A1 | 6/2002 | Albers et al. |
| 2003/0042205 A1 | 3/2003 | Gaudet et al. |
| 2003/0060361 A1 | 3/2003 | Chen et al. |
| 2003/0118581 A1 | 6/2003 | Sonobe et al. |
| 2003/0157014 A1 | 8/2003 | Wang et al. |
| 2003/0161781 A1 | 8/2003 | Cabasso et al. |
| 2003/0215640 A1 | 11/2003 | Ackerman et al. |
| 2004/0028901 A1 | 2/2004 | Rumpf et al. |
| 2004/0118287 A1 | 6/2004 | Jaffe et al. |
| 2004/0219363 A1 | 11/2004 | Schuch et al. |
| 2005/0150835 A1 | 7/2005 | Vo |
| 2005/0207962 A1 | 9/2005 | Dietz et al. |
| 2005/0247635 A1 | 11/2005 | Vo et al. |
| 2007/0203284 A1 | 8/2007 | Schuch et al. |
| 2007/0265161 A1 | 11/2007 | Gadkaree et al. |
| 2007/0287845 A1 | 12/2007 | Lilga et al. |
| 2008/0031972 A1 | 2/2008 | Sonobe et al. |
| 2008/0063591 A1 | 3/2008 | Im et al. |
| 2008/0132408 A1 | 6/2008 | Mitchell et al. |
| 2009/0208751 A1 | 8/2009 | Green et al. |
| 2009/0209418 A1 | 8/2009 | Watanabe et al. |
| 2010/0069507 A1 | 3/2010 | Tabata et al. |
| 2010/0173772 A1 | 7/2010 | Robinson et al. |
| 2010/0212495 A1 | 8/2010 | Gadkaree et al. |
| 2010/0298134 A1 | 11/2010 | De Leede et al. |
| 2011/0011414 A1 | 1/2011 | Hummel et al. |
| 2011/0175024 A1 | 7/2011 | Lang et al. |
| 2011/0244012 A1 | 10/2011 | Iida et al. |
| 2011/0306790 A1 | 12/2011 | Murphy et al. |
| 2012/0007027 A1 | 1/2012 | Istvan et al. |
| 2012/0204719 A1 | 8/2012 | Dubois-Brugger et al. |
| 2012/0289755 A1 | 11/2012 | Kato et al. |
| 2012/0292794 A1 | 11/2012 | Prabhu et al. |
| 2013/0211146 A1 | 8/2013 | Menne et al. |
| 2013/0281581 A1 | 10/2013 | Wong et al. |
| 2013/0295462 A1 | 11/2013 | Atanassova et al. |
| 2013/0310253 A1 | 11/2013 | Tabata et al. |
| 2013/0310605 A1 | 11/2013 | Salem et al. |
| 2014/0011666 A1 | 1/2014 | Yoshizaki et al. |
| 2014/0037536 A1 | 2/2014 | Reimerink-Schats et al. |
| 2014/0120339 A1 | 5/2014 | Nikova et al. |
| 2014/0267515 A1 | 9/2014 | Zhang et al. |
| 2014/0287306 A1 | 9/2014 | Takeshi et al. |
| 2015/0041708 A1 | 2/2015 | Wiesner et al. |
| 2015/0314273 A1* | 11/2015 | Paulus ............ B01J 35/002 502/324 |

FOREIGN PATENT DOCUMENTS

| | | |
|---|---|---|
| CN | 103107319 A | 5/2013 |
| CN | 103848802 A | 11/2014 |
| DE | 202006001770 U1 | 2/2007 |
| EP | 0484176 A1 | 5/1992 |
| EP | 0729785 A1 | 9/1996 |
| EP | 0862596 B1 | 6/2001 |
| EP | 0815566 B1 | 6/2006 |
| EP | 1757362 B1 | 2/2007 |
| EP | 1567602 B1 | 8/2007 |
| EP | 2045223 A1 | 4/2009 |
| EP | 2060535 A1 | 5/2009 |
| EP | 2308591 A1 | 4/2011 |
| EP | 2429020 A1 | 3/2012 |
| EP | 2478957 A1 | 7/2012 |
| EP | 2497751 A1 | 9/2012 |
| EP | 2674214 A1 | 12/2013 |
| EP | 2728407 A1 | 5/2014 |
| GB | 828206 A | 2/1960 |
| GB | 1045694 | 10/1996 |
| JP | S60225639 A | 11/1985 |
| JP | H0549921 A | 3/1993 |
| JP | H072951 B2 | 1/1995 |
| JP | H111100524 A | 4/1999 |
| JP | 2003201417 A | 7/2003 |
| JP | 3746509 B1 | 2/2006 |
| JP | 2007284337 A | 11/2007 |
| JP | 2010269994 A | 12/2010 |
| JP | 2011042569 A | 3/2011 |
| JP | 2014072497 A | 4/2014 |
| JP | 5629578 B2 | 11/2014 |
| WO | 9621698 | 7/1996 |
| WO | 9747691 A1 | 12/1997 |

(56) References Cited

FOREIGN PATENT DOCUMENTS

| WO | 9912641 A1 | 3/1999 |
|---|---|---|
| WO | 9923174 A1 | 5/1999 |
| WO | 9931175 A1 | 6/1999 |
| WO | 9951690 A1 | 10/1999 |
| WO | 9963007 A1 | 12/1999 |
| WO | 2000022051 A1 | 4/2000 |
| WO | 2002018929 A1 | 3/2002 |
| WO | 2002072258 A1 | 9/2002 |
| WO | 02083559 A1 | 10/2002 |
| WO | 03009927 A1 | 2/2003 |
| WO | 03020639 A1 | 3/2003 |
| WO | 03041847 A1 | 5/2003 |
| WO | 03070662 A1 | 8/2003 |
| WO | 03072352 A1 | 9/2003 |
| WO | 03072640 A2 | 9/2003 |
| WO | 2003099940 A1 | 12/2003 |
| WO | 2004076360 A1 | 9/2004 |
| WO | 2007070455 A1 | 6/2007 |
| WO | 2008133520 A1 | 11/2008 |
| WO | 2009011590 A1 | 1/2009 |
| WO | 2009088540 A1 | 7/2009 |
| WO | 2009105172 A2 | 8/2009 |
| WO | 2010008072 A1 | 1/2010 |
| WO | 2010144862 A2 | 12/2010 |
| WO | 2012102610 A1 | 8/2012 |
| WO | 2013045894 A1 | 4/2013 |
| WO | 2014070987 A1 | 5/2014 |
| WO | 2014091447 A1 | 6/2014 |
| WO | 2014141619 A1 | 9/2014 |
| WO | 2015168327 A1 | 11/2015 |

OTHER PUBLICATIONS

Asbury Carbons, Product Data Sheet 5991R, Carbon Black Powder, Asbury Graphite Mills, Inc., 405 Old Main Street, Asbury, NJ 08802, Revised Aug. 15, 2007, 1 page.
Asbury Carbons, Product Data Sheet 5379, Carbon Black Powder, Asbury Graphite Mills, Inc., 405 Old Main Street, Asbury, NJ 08802, Revised Mar. 10, 2011, 1 page.
Asbury Carbons, Product Data Sheet 5368, Carbon Black Powder, Asbury Graphite Mills, Inc., 405 Old Main Street, Asbury, NJ 08802, Revised Jun. 22, 2011, 1 page.
Asbury Carbons, Product Data Sheet 5303, Carbon Black Powder, Asbury Graphite Mills, Inc., 405 Old Main Street, Asbury, NJ 08802, Revised Sep. 14, 2012, 1 page.
Asbury Carbons, Product Data Sheet 5302, Carbon Black Beads, Asbury Graphite Mills, Inc., 405 Old Main Street, Asbury, NJ 08802, Revised Sep. 14, 2012, 1 page.
Attension, Theory Note 7, "Influence of Surface Roughness of Contact Angle and Wettability," Attension Biolin Scientific, Tietäjäntie 2, FIN-02130 Espoo, Finland, No Date Available, 3 pages.
NATROSOL® Hydroxyethylcellulose, A Nonionic Water-Soluble Polymer, Physical and Chemical Properties, Hercules Incorporated, Aqualon Division, 1313 North Market Street, Wilmington, DE 19894-0001, 250-11G Rev. 8-99 2M, 24 pages.
Turner, H.W., et al., "High-Throughput Heterogeneous Catalyst Research," 2009, Surface Science, 603:1763-1769.
Patent Abstracts of Japan, JPS60-225639, published Nov. 9, 1985, 1 page.
Bathey, B.R., et al., "Review Solar-Grade Silicon," 1892, J Mat Sci, 17:3077-3096.
Bin, D., et al., "Controllable Oxidation of Glucose to Gluconic Acid and Glucaric Acid Using an Electrocatalytic Reactor," 2014, Electrochimica Acta, 130:170-178. 9 pages.
Önal, Y., et al, "Structure Sensitivity and Kinetics of D-Glucose Oxidation to D-Gluconic Acid Over Carbon-Supported Gold Catalysts," 2004, J Catalysis, 223:122-133. 12 pages.
Colmenares, J.C., et al., "Heterogeneous Photocatalytic Nanomaterials: Prospects and Challenges in Selective Transformations of Biomass-Derived Compounds," 2014, Chem Soc. Rev., 43:765-778, 14 pages.
Delidovich, I.V., et al., "Selective Oxidation of Glucose Over Carbon-Supported Pd and Pt Catalysts," 2010, Catal Lett, 140:14-21, 8 pages.
Antolini, E., "Carbon Supports for Low-Temperature Fuel Cell Catalysts," 2009, Applied Catalysis B: Enviommental 38:1-24.
Barrett, E.P., et al., "The Determination of Pore Volume and Area Distributions in Porous Substances. I. Computations from Nitrogen Isotherms," 1951, The Volume and Area Distributions in Porous Substances, 373-380.
Brunauer, S., et al., "Adsorption of Gases in Multimolecular Layers," 1938, JACS, 60:309-319.
Dapsens, P.Y, et al., "Biobased Chemicals from Conception Toward Industrial Reality: Lessons Learned and To Be Learned," 2012, ACS Catal, 2:1487-1499.
Gerspacher, M., Dr., "Furnace Black Characterization," Presentation at the Non-Platinum Electrocatalysts Workshop held Mar. 21-22, 2003 in New Orleans, Louisiana, Sid Richardson Carbon Co., Fort Worth, Texas, 19 pages.
Haber, J., "Manual on Catalyst Characterization," 1991, International Union of Pure and Applied Chemistry, Physical Chemistry Division Commission on Colloid and Surfactant Chemistry Including Catalysis, Subcommittee on Catalyst Characterization, Pure & Appl Chem, 63/9:1227-1246.
Hidayu, A.R., et al., "Characterization of Activitated Carbon Prepared from Oil Palm Empty Fruit Bunch Using BET and FT-IR Techniques," 2013, Procedia Engineering, 68: 379-387.
Kishimoto, H., et al., "Amorphous Alloy Electrodes for Electro-oxidation of Propane," 1995, Sci Rep RITU A41, 83-88, 6 pages.
Kruk, M., et al., "Well-Defined Polyethylene Oxide-Polyacrylonitrile Di-Block Copolymers as Templates for Meso Porous Silicas and Precursors for Meso Porous Carbons," 2006 Chem Mater, 18/6:1417-1424.
Liu, D., et al., "Preparation of Activated Carbon Aerogels with Hierarchically Porous Structures for Electrical Double Layer Capacitors, 2013," Electrochimica Acta, 89:571-576.
Norman, D.T., "Rubber Grade Carbon Blacks," Witco Coporation, Concarb Division, Houston, Texas, 2001, 19 pages.
Walker, P.L. Jr., "Carbon—A Versatile Catalyst Support," 1978, Fifth London International Carbon and Graphite Conference, Imperial College, London, Sep. 18-22, 1978, vol. 3, 10 pages.
Yang, C-M., et al., "Desalination Effects of Capacitive Deionization Process with Porous Carbon-Nano Materials," 2004, Kongop Hwahak, 15/3:294-299 (CAPLUS Abstract Only).
Handbook of Pharmaceutical Catalysis, Johnson Matthey Catalysts, 2009, Johnson Matthey Plc, 108 pages.
IARC Monographs on the Evaluation of Carcinogenic Risks to Humans, vol. 93, Carbon Black, Titanium Dioxide, and Talc, World Health Organization, 2010, pp. 43-191.
Insights on Carbon Black Fundamentals, 2006, 8 pages, obtained from www.moderndispersions.com/CARBON_20BLACK_20FUNDAMENTALS.pdf.
English Language Abstract of JPS62223125A, 1987, 1 page.
English Language Abstract of JPS5818418A, 1983, 2 pages.
WO2007132936A1, English Language Abstract, 2007, 1 page.
Sokhi, R.S., et al., "PIXE Analysis of Carbon Black for Elemental Impurities," 1990, 7b Nuclear Instruments & Methods in Physics, vol. B49, No. 1/4:414-417, 4 pages.

* cited by examiner

POROUS SHAPED METAL-CARBON PRODUCTS

CROSS REFERENCE TO RELATED APPLICATIONS

This application is a division of U.S. application Ser. No. 15/132,048, filed Apr. 18, 2016, which claims the benefit of U.S. provisional application No. 62/247,727, filed Oct. 28, 2015, the entire disclosures of which are incorporated herein by reference.

FIELD OF THE INVENTION

The present invention provides a novel porous metal-containing carbon-based material, and related methods and compositions. The materials are particularly suited for use as catalyst materials.

BACKGROUND

Renewable raw materials such as sugar and its derivatives are attractive feedstock sources for potential use in the production of commodity chemicals because they are relatively abundant and cheap. Most of these materials are water soluble and can be processed in aqueous solutions. These natural materials contain a lot of oxygen which needs to be eliminated during processing. Usually it can be done by catalytic hydrogenation which removes extra oxygen in the form of water. Long term catalyst stability is a necessity for commodity chemical production, meaning that the catalyst must be stable, productive, and selective under commercial reaction conditions for long periods of time.

One of the cheapest and most available catalysts for this kind of treatment is metal supported on a mineral carrier, which can be used in fixed bed applications. However, catalysts supported on mineral carriers have low stability in aqueous media due to slow support dissolution. A need, therefore, exists for new materials that can be commercially produced and that are stable in applications requiring use in an aqueous environment. Such materials would be useful in catalytic applications, as well as other applications requiring long term use under aqueous conditions.

SUMMARY OF THE INVENTION

In one aspect, the present invention provides a process for preparing a porous, shaped metal-carbon product, the process comprising:

mixing a carbonaceous material with water, a water-soluble organic binder, and a (first) metal precursor to form a metal-carbon mixture, wherein the metal precursor is a compound selected from the group consisting of a metal carbonate, a metal oxide, a metal hydroxide, a salt of a metal acid, a heteropoly acid, a metal carboxylate, a metal carbide, a metal chloride, a metal amine complex-containing compound, a hydrate thereof, and a mixture of any two or more thereof;

shaping the metal-carbon mixture to form a green, shaped metal-carbon product; and heating the green, shaped metal-carbon product to a carbonization temperature to produce a carbonized, shaped metal-carbon product comprising a plurality of pores.

In another aspect, the present invention provides porous, shaped metal-carbon products produced by the processes described herein.

In a further aspect, the present invention provides a process for producing bis-hydroxymethyltetrahydrofuran (BHMTHF) from 2,5-bis-hydroxymethylfuran (BHMF), the process comprising:

contacting BHMF with hydrogen in the presence of a hydrogenation catalyst comprising a porous, shaped metal-carbon product of the present invention to produce BHMTHF.

In a still further aspect, the present invention provides a process for producing a $C_3$-$C_6$ diol from a corresponding $C_3$-$C_6$ polyol, the process comprising:

contacting a $C_3$-$C_6$ polyol with hydrogen in the presence of a hydrodeoxygenation catalyst comprising a porous, shaped metal-carbon product of the present invention to produce a corresponding $C_3$-$C_6$ diol.

In another aspect, the present invention provides a process for producing 1,6-hexamethylenediamine (HMDA) from 1,6-hexanediol (HDO), the process comprising:

contacting HDO with an amine in the presence of an amination catalyst comprising a porous, shaped metal-carbon product of the present invention to form HMDA.

In a further aspect, the present invention provides a process for producing glucaric acid from glucose, the process comprising:

contacting glucose with oxygen in the presence of an oxidation catalyst comprising a porous, shaped metal-carbon product of the present invention to form glucaric acid.

In a still further aspect, the present invention provides a process for producing a dicarboxylic acid from an aldaric acid, or salt, ester, or lactone thereof, the process comprising:

contacting an aldaric acid, or salt, ester or lactone thereof with hydrogen in the presence of a halogen-containing compound and a hydroxygenation catalyst comprising a porous, shaped metal-carbon product of the present invention to form a dicarboxylic acid.

In yet a still further aspect, the present invention provides a process for producing 2,5-bis-hydroxymethylfuran (BHMF) from 5-hydroxymethylfurfural (HMF), the method comprising:

contacting HMF with hydrogen in the presence of a hydrogenation catalyst comprising a porous, shaped metal-carbon product of the present invention to form BHMF.

DETAILED DESCRIPTION OF THE INVENTION

The present invention provides a novel porous metal-containing carbon-based material (i.e., products) having desirable properties. The materials exhibit certain properties of the metal components from which they are prepared. The durable porous materials are particularly suitable for use as a catalyst, as well as other applications in need of mechanically strong, metal-containing materials.

In one embodiment, the present invention provides a process for preparing a carbonized shaped metal-carbon product, the method comprising:

mixing a carbonaceous material with water, a water-soluble organic binder, and a metal precursor to form a metal-carbon mixture, wherein the metal precursor is a compound selected from the group consisting of a metal carbonate, a metal oxide, a metal hydroxide, a salt of a metal acid, a heteropoly acid, a metal carboxylate, a metal carbide, a metal chloride, a metal amine complex-containing compound, a hydrate thereof, and a mixture of any two or more thereof;

shaping the metal-carbon mixture to form a green, shaped metal-carbon product and heating the green, shaped metal-carbon product to a carbonization temperature to produce a carbonized shaped metal-carbon product comprising a plurality of pores (i.e., the "carbonization step").

Applicants have discovered that porous, carbonized, shaped metal-carbon products produced by the processes described herein exhibit certain properties of the metal despite the metal precursor being mixed with other components of the metal-carbon mixture and subsequently carbonized together with these other components. This effect is particularly apparent when the products are used as catalysts. As a catalytic material, performance was comparable to, if not better than, a catalyst prepared by impregnating (and thus depositing metal onto the surfaces of) a mineral oxide-based support with metal, as demonstrated in Example 5, hereinbelow.

The examples also demonstrate that metal precursors employed in the practice of the present invention do not have to be water-soluble to achieve this effect. They may be water-insoluble. One significance of a process that can produce a porous, metal-containing, carbon-based product that exhibits certain properties of the metal which can be prepared, not only from water-soluble metal precursors, but also from water-insoluble metal precursors, is that much higher metal loadings can be achieved as compared to metal loadings that are achieved using standard processes, such as, for example impregnation processes. This is because higher metal loadings can be achieved in a single step without changing the functional form of the support material, which might otherwise impact accessibility to the pores.

The processes of the present invention enable the incorporation of a wide variety of metal types in/onto carbon that would otherwise be challenging using more commonly used metal precursors such as metal nitrates. While metal nitrates, which are strong oxidants, can be heated with mineral oxide materials to impregnate them without consequence, attempting to use the same process to impregnate carbon on a large scale may be a potentially hazardous endeavor.

In situ reduction of metal precursor to metal during the carbonization step for certain metal precursors is an additional advantage of the process as it eliminates the need for a subsequent reduction process. Without wishing to be bound by theory, it is believed that during the carbonization step, the metal precursor may decompose, and in certain cases, be reduced to a metal. The resulting carbonized product exhibits catalytic activity, as demonstrated by the studies described in the Examples. This suggests that the metal decomposition products are not only in a catalytically active form, but that they are accessible (i.e., located on the surfaces (external/internal)) to the reactants.

A further advantage of the processes of the present invention is that the product is relatively "clean" with respect to the absence of potential contaminants, such as, for example, a halide (when a metal halide is not utilized as the metal precursor), which might otherwise need to be washed out before use in certain applications.

Metal precursors that are employed in the practice of the present invention may comprise a variety of metals. The metals may be a base metal or a noble metal. As used herein, the term "base metal" refers to a metal that is not a noble metal. The term, "noble metal" is used herein to refer to Ru, Rh, Pd, Ag, Os, Ir, Pt, or Au.

In some embodiments, the metal is selected from groups IV, V, VI, VII, VIII, IX, X, XI, XII, and XIII. In various embodiments, the metal is a d-block metal. Exemplary d-block metals include, for example, Ni, Co, W, Cu, Zn, Fe, Mo, Ni, Rh, Pd, Ag, Os, Ir, Pt, Au, and the like.

In other embodiments, the metal precursor comprises a metal selected from the group consisting of Cu, Pb, Ni, Zn, Fe, Mo, Al, Sn, W, Ta, Co, Bi, Cd, Ti, Zr, Sb, Mn, Be, Cr, Ge, V, Ga, Hf, In, Nb, Rh, Tl, Ru, Rh, Pd, Ag, Os, Ir, Pt, or Au. Often, the metal precursor comprises a metal that is a base metal. In specific embodiments, the metal precursor comprises a metal selected from the group consisting of Cu, Pb, Ni, Zn, Fe, Mo, Al, Sn, W, Ta, Co, Bi, Cd, Ti, Zr, Sb, Mn, Be, Cr, Ge, V, Ga, Hf, In, Nb, Rh, and Tl. In some embodiments, the metal precursor comprises a metal selected from the group consisting of Ni, Co, Mo, Nb, and W. Often, the metal precursor comprises a metal selected from the group consisting of Ni and W.

The processes of the present invention can employ a variety of types of metal precursors, including a metal carbonate, a metal oxide, a metal hydroxide, a salt of a metal acid, a heteropoly acid, a metal carboxylate, a metal carbide, a metal chloride, a metal amine complex-containing compound, as well as hydrates thereof and mixtures of any two or more thereof. As explained above, the metal precursor may be water-soluble or water-insoluble. As used herein the term "water-insoluble" when used in connection with the metal precursor, refers to a metal precursor having a solubility of less than 0.1 wt % in water. The term "water-soluble", when used in connection with the metal precursor, refers to a metal precursor having a solubility of 0.1 wt % or greater in water.

Metal carbonates that are suitable for use in the practice of the present invention include $NiCO_3$, and the like, metal hydroxycarbonates, such as, for example $NiCO_3.2Ni(OH)_2.xH_2O$, and the like. Also suitable are metal amine complexes, such as, for example, tetraaminenickel carbonate $(Ni(NH_3)_4(CO_3))$, tetraaminecobalt carbonate $(Co(NH_3)_4CO_3)$, and the like. Suitable metal oxides include, for example, $NiO$, $WO_3$, $CoO$, $Co_3O_4$, $Co_2O_3$, and the like. Metal hydroxides that are suitable for use in the practice of the present invention include, for example, $Ni(OH)_2$, $Co(OH)_2$, $W(OH)_2$, and the like. Exemplary salts of metal acids that are suitable for use in the processes of the present invention include, for example, a tungstate (e.g., a hydrogentungstate, a polymeric $W_2O_7^{2-}$, a paratungstate A $([W_7O_{24}]^{6-})$, a paratungstate B $([H_2W_{12}O_{42}]^{10-})$, a meta-tungstate ($\alpha$-$[H_2W_{12}O_{40}]^{6-}$, tungstate Y $([W_{10}O_{32}]^{4-})$, tungstate X ($\beta$-$[H_2W_{12}O_{40}]^{6-}$), and the like, and hydrates thereof). The salt of the metal acid may be first formed by premixing a metal acid or metal oxide (e.g., $H_2WO_4$, $WO_3$, and the like) with a base (e.g., $NH_3$, a diamine (e.g., ethylene diamine, KOH, NaOH, and the like) to form the corresponding metal salt in an aqueous solution that can be introduced into the ensuing metal-carbon mixture. Exemplary metal salts that can be formed in such manner include, for example, $(NH_3)_2WO_4$, $K_2WO_4$, $(C_2H_8N_2)_2WO_4$, and the like. Heteropoly acids that are suitable for use in the practice of the present invention include tungstosilicic acid hydrate $(H_4[Si(W_3O_{10})_4].xH_2O)$, phosphotungstic acid hydrate $(H_3[P(W_3O_{10})_4].xH_2O)$, silicomolybdic acid $(H_4SiO_4.12MoO_3)$. Exemplary metal carboxylates that are suitable for use as a metal precursor in the present invention include metal formates, metal acetates, metal citrates, metal succinates, metal oxalates, metal lactates, and the like. Specific examples include Cobalt (III) 2-ethylhexanoate, Cobalt (II) 2-ethylhexanoate $([CH_3(CH_2)_3CH(C_2H_5)CO_2]_2Co)$, Nickel (II) 2-ethylhexanoate $([CH_3(CH_2)_3CH(C_2H_5)CO_2]_2Ni)$, Nickel(II) acetate tetrahydrate $(Ni(OCOCH_3)_2.4H_2O)$, Nickel (III) oxalate dihydrate ($NiC_2O_4 \cdot 2H_2O$), Cobalt (III) oxalate dihydrate ($CoC_2O_4 \cdot 2H_2O$), and the like. Exemplary metal carbides that are suitable for use in the practice of the present invention include, for example, tungsten carbide (WC), and the like. Metal chlorides that are suitable for use in the practice of the present invention include nickel chloride ($NiCl_2$), and the like. The term "metal amine complex-containing compound" refers herein to a compound that has a metal complex containing at least one ammonia ($NH_3$) ligand complexed with a metal ion, and typically, a counterion. Typical counterions include, for example carbonate (including, e.g., a bicarbonate), a halide, a hydroxide, a carboxylate, and the like. In certain embodiments, the metal precursor comprises metal that has a melting temperature greater than the carbonization temperature.

A preferred nickel-based precursor is nickel carbonate and hydrates thereof. Preferred tungsten-based precursors include salts of tungstic acid (i.e., where the tungsten is present in the form of a tungstate anion), such as, for example, ammonium paratungstate, ammonium metatungstate, and the like, and hydrates thereof, as well as solutions of tungsten trioxide ($WO_3$) or tungstic acid ($H_2WO_4$) in base (e.g., ammonia (NH3), an amine hydroxide, and the like.

The quantity of metal precursor utilized in the metal-carbon mixture will vary depending on the quantity of metal desired in the carbonized, shaped metal-carbon product. Those having ordinary skill in the art will be able to readily compute the quantity of metal precursor required to achieve the desired target wt % of metal in the carbonized, shaped metal-carbon product. In some embodiments, the quantity of metal precursor utilized in the metal-carbon mixture is in the range of from about 1 wt % to about 90 wt %, and more typically in the range of from about 1 wt % to about 85 wt %, from about 1 wt % to about 80 wt %, from about 1 wt % to about 75 wt %, from about 1 wt % to about 70 wt %, from about 1 wt % to about 65 wt %, from about 1 wt % to about 60 wt %, from about 1 wt % to about 55 wt %, from about 1 wt % to about 50 wt %, from about 1 wt % to about 45 wt %, from about 1 wt % to about 40 wt %, from about 1 wt % to about 35 wt %, from about 1 wt % to about 30 wt %, from about 1 wt % to about 25 wt %, or from about 1 wt % to about 20 wt %. In other embodiments, the quantity of metal precursor in the metal-carbon mixture is in the range of from about 5 wt % to about 70 wt %, from about 10 wt % to about 70 wt %, from about 15 wt % to about 70 wt %, from about 5 wt % to about 60 wt %, from about 10 wt % to about 60 wt %, from about 15 wt % to about 60 wt %, from about 20 wt % to about 60 wt %, or from about 25 wt % to about 60 wt %. Often, the quantity of metal precursor in the metal-carbon mixture is in the range of from about 1 wt % to about 25 wt %, from about 2 wt % to about 25 wt %, from about 3 wt % to about 25 wt %, from about 4 wt % to about 25 wt %, from about 5 wt % to about 25 wt %, or from about 5 wt % to about 20 wt %. In some embodiments, such as, for example, when the metal is a promoter, the quantity of corresponding metal precursor in the metal-carbon mixture is in the range of from about 0.1 wt % to about 10 wt %, from about 0.1 wt % to about 5 wt %, or from about 0.5 wt % to about 5 wt %.

Water-soluble organic binders that are suitable for use in the practice of the present invention are water-soluble organic compounds that are capable of being carbonized at a temperature in the range of from about 250° C. to about 1000° C., and which exhibit a solubility of at least about 1 wt % in water at a temperature of 50° C. In some embodiments, the water-solubility binder exhibits a solubility of at least about 2 wt % at a temperature of 50° C.

Water-soluble organic binders employed in the practice of the present invention are water-soluble organic compounds that typically contain only carbon, oxygen, and hydrogen atoms. In some embodiments, however, the water-soluble organic binder may contain other atom species. Suitable water-soluble organic binders are either a carbohydrate or derivative thereof, or a non-carbohydrate compound. The carbohydrate employed in the practice of the present invention may be a monosaccharide, a disaccharide, an oligosaccharide, a polysaccharide, or derivative thereof. Monosaccharides that are suitable for use in the practice of the present invention include, for example, glucose, fructose, galactose, ribose, and the like. Suitable disaccharides include, for example, sucrose, lactose, maltose, trehalose, and the like. Often, the water-soluble organic binder comprises a sugar (i.e., a monosaccharide and/or a disaccharide), either alone, or together with a water-soluble polymer. Exemplary oligosaccharides that are suitable for use in the practice of the present invention include fructo-oligosaccharides, galacto-oligosaccharides, mannan oligosaccharides, and the like.

Exemplary polysaccharides include, for example, a cellulose (such as, for example, methylcellulose, ethylcellulose, ethylmethylcellulose, hydroxyethylcellulose, hydroxypropylcellulose, methylhydroxyethylcellulose, ethylhydroxyethylcellulose, hydroxypropylmethylcellulose, carboxymethylcellulose, and the like, as well as mixtures thereof), alginic acid, pectin, an aldonic acid, and the like, and mixtures thereof.

Suitable carbohydrate derivatives include, for example, polyols (e.g., sugar alcohols, such as, for example, sorbitol, glycerol, erythritol, threitol, arabitol, xylitol, ribitol, mannitol, galactitol, fucitol, iditol, inositol, volemitol, isomalt, maltitol, lactitol, maltotritol, maltotetraitol, polyglycitol, and the like); sugar acids (e.g., gluconic acid, glucoronic acid, and the like), amino sugars (e.g., glucosamine, and the like), sialic acid, and the like.

Water-soluble non-carbohydrate compounds that are suitable for use in the practice of the present invention include, for example, a water-soluble non-carbohydrate polymer, a water-soluble fatty acid or salt thereof, a water-soluble fatty alcohol or ester thereof, and the like.

Water-soluble non-carbohydrate polymers that may be employed as a binder in the present invention include homopolymers, copolymers (or other multi-monomer species-based polymer, e.g., polypeptides, polynucleotides, collagen, gelatin, and the like), hydrogel-forming polymers, and the like. Suitable non-carbohydrate polymers include, for example, polyacrylic acids, polyvinylalcohols, polyvinylpyrrolidones, polyvinyl acetate, polyacrylates, polyethers (such as, for example, a polyethylene glycol, and the like), polyols (e.g., glycerol, and the like), polyethylene oxides, poly-oxo-methlene, polyvinylphthalate, Gum arabic, phenolic resin solutions, polyacrylamides, polylactic acids, and the like, as well as mixtures and copolymers thereof. Suitable co-polymers include, for example, polylactic-co-glycolic acid, and the like.

In some embodiments, the water-soluble organic binder comprises a water-soluble polymer having a relatively low number average molecular weight and/or is capable of yielding relatively low viscosity solutions. Accordingly, in various embodiments, the binder comprises a water soluble polymer, wherein a 2 wt % aqueous solution or a 5 wt % aqueous solution of the water-soluble polymer has a viscosity of no greater than about 500 mPa-s, or no greater than about 400 mPa-s, or no greater than about 300 mPa-s, or no greater than about 200 mPa-s, or no greater than about 100 mPa-s, or no greater than about 75 mPa-s, or no greater than about 50 mPa-s at 25° C. and/or the water soluble polymer has a number average molecular weight (Mn) that is no greater than about 50,000 g/mole, or no greater than about 40,000 g/mol, or no greater than about 30,000 g/mol, or no greater than about 25,000 g/mol, or no greater than about 20,000 g/mol. In some embodiments, the binder comprises a water-soluble polymer, wherein a 2 st % aqueous solution or a 5 wt % aqueous solution of the water-soluble polymer has a viscosity that is in the range of from about 2 to about 500 mPa-s, from about 2 to about 400 mPa-s, from about 2 to about 100 mPa-s, from about 2 to about 75 mPa-s, or from about 2 to about 50 mPa-s at 25° C.

In these and other embodiments, the water-soluble polymer can have a number average molecular weight (Mn) that is in the range of from about 2,000 to about 50,000 g/mol, from about 5,000 to about 40,000 g/mol, from about 5,000 to about 30,000 g/mol, from about 5,000 to about 25,000 g/mol, from about 5,000 to about 20,000 g/mol, from about 20,000 to about 50,000 g/mol, from about 10,000 to about 40,000 g/mol, from about 10,000 to about 30,000 g/mol, from about 10,000 to about 25,000 g/mol, or from about 10,000 to about 20,000 g/mol. Water-soluble organic binders that are suitable for use in the practice of the present invention include those described in published PCT application WO 2015/168327, as well as U.S. applications U.S. Ser. No. 62/247,721 and U.S. Ser. No. 15/131,829, each of which is incorporated herein by reference The quantity of binder employed in the metal-carbon mixture is typically in the range of from about 10 wt % to about 50 wt %. In some embodiments, the quantity of binder is in the range of from about 10 wt % to about 45 wt %, from about 15 wt % to about 40 wt %, from about 20 wt % to about 35 wt %, or from about 25 wt % to about 35 wt %.

One of ordinary skill will appreciate that the binder may be a mixture of the above-described compounds. For example, in certain embodiments, the binder comprises at least one monosaccharide or disaccharide, and at least one polysaccharide. In these embodiments, the weight ratio of mono- or di-saccharide to polysaccharide is typically in the range of from about 2:1 to about 30:1. More typically, the weight ratio is from about 3:1 to about 25:1, from 3:1 to about 20:1, from about 5:1 to about 20:1, or from about 10:1 to about 20:1. In a preferred embodiment, the binder comprises a mixture of glucose and a cellulose, such as, for example, hydroxyethylcellulose.

As used herein, the term "carbonaceous material" refers to elemental carbon in the form of graphite or an amorphous form of carbon. When the carbonaceous material employed in the practice of the present invention is an amorphous carbon, it is typically a carbon black or an activated carbon. The choice of carbonaceous material will depend on the desired properties for the metal-containing carbon composite material. It has been discovered that the porous nature of the underlying carbonaceous material corresponds substantially to the corresponding properties in the (carbonized) metal-containing carbon composite material.

Accordingly, when a relatively low porosity, low specific surface area composite material is desired, carbon black is typically employed. When a relatively high porosity, high specific surface area composite material is desired, activated carbon is typically utilized. In some embodiments, it may be desired to use carbon nanotubes as the carbonaceous material. In certain applications, e.g., when a highly electrically-conductive material is desired, it may be desired to use graphite as the carbonaceous material. The foregoing carbonaceous materials are readily available from commercial suppliers. Specific carbon blacks that are suitable for use in the processes of the present invention include those described in published PCT application WO 2015/168327, as well as U.S. applications U.S. Ser. No. 62/247,721 and U.S. Ser. No. 15/131,829, each of which is incorporated herein by reference.

The weight ratio of binder to carbonaceous material in the metal-carbon mixture is typically at least about 1:4, at least about 1:3, at least about 1:2, at least about 1:1, or at least 1.5:1. The weight ratio of binder to carbonaceous material in the metal-carbon mixture can also be from about 1:4 to about 3:1, from about 1:4 to about 1:1, from about 1:3 to about 2:1, from about 1:3 to about 1:1, or about 1:1. Typically, the quantity of carbonaceous material in the metal-carbon mixture is at least about 35 wt % or more such as at least about 40 wt %, at least about 45 wt %, as at least about 50 wt %, as at least about 55 w. %, at least about 60 wt %, at least about 65 wt %, or at least about 70 wt % on a dry weight basis. In various embodiments, the quantity of carbonaceous material in the metal-carbon mixture is from about 35 wt. % to about 80 wt %, from about 35 wt % to about 75 wt %, from about 40 wt % to about 80 wt %, or from about 40 wt % to about 75 wt % on a dry weight basis.

The metal-carbon mixture typically comprises a quantity of carbonaceous material in the range of from about 10 wt % to about 80 wt %, and more typically in the range of from about 15 wt % to about 75 wt %, from about 15 wt % to about 70 wt %, from about 15 wt % to about 65 wt %, from about 15 wt % to about 60 wt %, from about 15 wt % to about 55 wt %, from about 15 wt % to about 50 wt %, from about 15 wt % to about 45 wt %, from about 15 wt % to about 40 wt %, from about 15 wt % to about 35 wt %, from about 20 wt % to about 70 wt %, from about 20 wt % to about 65 wt %, from about 20 wt % to about 60 wt %, from about 20 wt % to about 55 wt %, from about 20 wt % to about 50 wt %, from about 20 wt % to about 45 wt %, from about 20 wt % to about 40 wt %, from about 20 wt % to about 35 wt %, or from about 25 wt % to about 35 wt %.

When a carbon black is used, it may be a non-conductive or a conductive carbon black. The carbon black materials used to prepare the shaped porous metal-carbon products of the present invention also generally have specific pore volumes greater than about 0.1 $cm^3/g$, greater than about 0.2 $cm^3/g$, or greater than about 0.3 $cm^3/g$. The specific pore volume of the carbon black materials may be in the range from about 0.1 $cm^3/g$ to about 1 $cm^3/g$, from about 0.1 $cm^3/g$ to about 0.9 $cm^3/g$, from about 0.1 $cm^3/g$ to about 0.8 $cm^3/g$, from about 0.1 $cm^3/g$ to about 0.7 $cm^3/g$, from about 0.1 $cm^3/g$ to about 0.6 $cm^3/g$, from about 0.1 $cm^3/g$ to about 0.5 $cm^3/g$, from about 0.2 $cm^3/g$ to about 1 $cm^3/g$, from about 0.2 $cm^3/g$ to about 0.9 $cm^3/g$, from about 0.2 $cm^3/g$ to about 0.8 $cm^3/g$, from about 0.2 $cm^3/g$ to about 0.7 $cm^3/g$, from about 0.2 $cm^3/g$ to about 0.6 $cm^3/g$, from about 0.2 $cm^3/g$ to about 0.5 $cm^3/g$, from about 0.3 $cm^3/g$ to about 1 $cm^3/g$, from about 0.3 $cm^3/g$ to about 0.9 $cm^3/g$, from about 0.3 $cm^3/g$ to about 0.8 $cm^3/g$, from about 0.3 $cm^3/g$ to about 0.7 $cm^3/g$, from about 0.3 $cm^3/g$ to about 0.6 $cm^3/g$, or from about 0.3 $cm^3/g$ to about 0.5 $cm^3/g$. Carbon black materials with these specific pore volumes provide a volume sufficient to provide uniform wetting and good dispersion of the catalytically active components while enabling sufficient contact between the reactant molecules and the catalytically active surface. Mean pore diameters and pore volumes are determined in accordance with the procedures described in E. P. Barrett, L. G. Joyner, P. P. Halenda, J. Am. Chem. Soc. 1951, 73, 373-380 (referred to herein as the "BJH method"), and ASTM D4222-03(2008) Standard Test Method for Determination of Nitrogen Adsorption and Desorption Isotherms of Catalysts and Catalyst Carriers by Static Volumetric Measurements, which are incorporated herein by reference.

Typically, the carbon black has a BET specific surface area in the range of from about 20 $m^2/g$ to about 500 $m^2/g$. In some embodiments, the BET specific surface area is in the range of from about 20 $m^2/g$ to about 350 $m^2/g$, from about 20 $m^2/g$ to about 250 $m^2/g$, from about 20 $m^2/g$ to about 225 $m^2/g$, from about 20 $m^2/g$ to about 200 $m^2/g$ from about 20 $m^2/g$ to about 175 $m^2/g$, from about 20 $m^2/g$ to about 150 $m^2/g$, from about 20 $m^2/g$ to about 125 $m^2/g$, or from about 20 $m^2/g$ to about 100 $m^2/g$, from about 25 $m^2/g$ to about 500 $m^2/g$, from about 25 $m^2/g$ to about 350 $m^2/g$, from about 25 $m^2/g$ to about 250 $m^2/g$, from about 25 $m^2/g$ to about 225 $m^2/g$, from about 25 $m^2/g$ to about 150 $m^2/g$, from about 25 $m^2/g$ to about 125 $m^2/g$, from about 25 $m^2/g$ to about 100 $m^2/g$, from about 30 $m^2/g$ to about 500 $m^2/g$, from about 30 $m^2/g$ to about 350 $m^2/g$ from about 30 $m^2/g$ to about 250 $m^2/g$, from about 30 $m^2/g$ to about 225 $m^2/g$, from about 30 $m^2/g$ to about 200 $m^2/g$, from about 30 $m^2/g$ to about 175 $m^2/g$, from about 30 $m^2/g$ to about 150 $m^2/g$, from about 30 $m^2/g$ to about 125 $m^2/g$, or from about 30 $m^2/g$ to about 100 $m^2/g$. As used herein, the term "BET specific surface area" refers to specific surface area as determined from nitrogen adsorption data in accordance with the method of Brunauer, Emmet and Teller, as described in *J. Am. Chem. Soc.* (1938) 60:309-331 and ASTM Test Methods D3663, D6556 or D4567 (Standard Test Methods for Surface Area Measurements by Nitrogen Adsorption), which are incorporated herein by reference.

In some embodiments, e.g., where a high surface area, metal-carbon product is desired, the carbonaceous material is an activated carbon. Activated carbons that are suitable for use in the practice of the present invention typically exhibit a BET specific surface area that is greater than 500 $m^2/g$. In some embodiments, the BET specific area of the activated carbon is in the range of from about 550 $m^2/g$ to about 3500 $m^2/g$. In certain embodiments, the BET specific surface area of the activated carbon is in the range of from about 600 $m^2/g$ to about 2500 $m^2/g$, from about 600 $m^2/g$ to about 2250 $m^2/g$, from about 600 $m^2/g$ to about 2000 $m^2/g$, or from about 700 $m^2/g$ to about 2000 $m^2/g$. In other embodiments, the BET specific surface of the activated carbon is in the range of from about 800 $m^2/g$ to about 2500 $m^2/g$, from about 800 $m^2/g$ to about 2000 $m^2/g$, or from about 1000 $m^2/g$ to about 2000 $m^2/g$.

In other embodiments, the carbonaceous material is a graphite. The graphite may be in either natural or synthetic form of fine grain, medium grain, or coarse grain grades. Typically, the graphite is synthetic graphite. Graphites that are suitable for use in connection with the present invention, are in powder form and have a bulk density that is greater than 1 $g/cm^3$, and more typically, the bulk density is greater than about 1.1 $g/cm^3$, and in some embodiments, greater than about 1.2 $g/cm^3$. Graphites employed in the practice of the present invention are typically porous, having a porosity in the range of from about 0.5 vol % to about 60 vol %, and more often in the range of from about 0.5 vol % to about 55 vol %.

In certain embodiments, the carbonaceous material is a mixture of any two or more forms of carbon selected from the group consisting of a carbon black, an activated carbon, and a graphite. Use of such mixtures allows one to achieve properties that are intermediate with respect to the properties associated with each individual form of carbon. For example, though graphite typically has a BET surface area of less than 20 $m^2/g$, use of a blend of graphite with carbon black or activated carbon in the appropriate relative quantities can result in a mixture having a BET surface area greater than 20 $m^2/g$.

The amount of water utilized in the metal-carbon mixture is typically in the range of from about 15 wt % to about 70 wt %. More typically, it is in the range of from about 15 wt % to about 65 wt %, from about 15 wt % to about 60 wt %, from about 15 wt % to about 55 wt %, from about 15 wt % to about 50 wt %, from about 15 wt % to about 45 wt %, from about 20 wt % to about 40 wt %, or from about 25 wt % to about 40 wt %.

In certain embodiments, the metal-carbon mixture comprises: from about 0.1 wt % to about 50 wt % metal precursor; from about 20 wt % to about 35 wt % carbonaceous material; from about 20 wt % to about 35 wt % monosaccharide or disaccharide; from about 0.5 wt % to about 5 wt % polysaccharide; and from about 25 wt % to about 45 wt % water.

The metal-carbon mixture may contain additives such as, for example forming aids (e.g., lubricants, such as, for example, waxes (e.g., stearic acid and salts thereof), and the like); wetting agents (e.g., surfactants); porogens; peptization agents; an organic solvent; and the like, as well as combinations of two or more thereof.

During the mixing step, the order of addition of the components is not critical. However, to facilitate ease of mixing, it may be desirable to premix certain components together prior to mixing all of the components together. For example, when the metal precursor is water-soluble, it may be pre-mixed with water and optionally, the water-soluble organic binder, prior to adding the carbonaceous material to the mixture. Typically, the water and water-soluble organic binder are premixed together to form a binder solution. In embodiments where the metal precursor is water-insoluble, it may be desirable to premix the metal precursor with the carbonaceous material, followed by mixing the resulting combined dry mix with binder solution.

The metal-carbon mixture may be heated to facilitate dissolution of soluble components during mixing, such as, for example, any water-soluble polymers. For example, in some embodiments, the metal-carbon mixture, or re-mixture of water and binder and optionally a water-soluble metal precursor are heated during the mixing step to a temperature of at least about 50° C., at least about 60° C., or at least about 70° C. In various embodiments, the water and binder can be heated to a temperature of from about 50° C. to about 95° C., from about 50° C. to about 90° C., or from about 60° C. to about 85° C. Mixing can be carried out using industrial mixers such as, for example, a mix muller, a planetary mixer, a drum mixer, a pan mixer, a twin shaft mixer, a cement mixer, or other type of mixer suitable for mixing high viscosity materials.

After the mixing step, the metal-carbon mixture is pliable and can be readily manipulated into a desired shape or form during a shaping step to form a green, shaped metal-carbon product. As used herein, the term "green shaped metal-carbon product" refers to the metal-carbon mixture or partially or fully dehydrated mixture thereof, formed into a desired shape, but not yet carbonized. During the shaping step, the metal-carbon mixture is converted into a desired shape using a method such as, for example, pressing, casting, injection molding, extruding, spreading as a paste, pelletizing, granulating, calendering, 3-D printing, and the like, and optionally subsequently breaking such shapes into smaller pieces (i.e., smaller shaped pieces). The shaping step may be carried out at an elevated temperature to reduce the viscosity of the mixture and corresponding forces required to manipulate the material into the desired shape. In some embodiments, the shaping step is carried out at a temperature of at least about 50° C., at least about 60° C., or at least about 70° C. In various embodiments, the shaping step is carried out at a temperature of from about 50° C. to about 95° C., from about 50° C. to about 90° C., or from about 60° C. to about 85° C. Suitable methods for shaping the metal-carbon mixture include those described in published PCT application WO 2015/168327, as well as U.S. applications U.S. Ser. No. 62/247,721 and U.S. Ser. No. 15/131,829 for forming or shaping a carbon black mixture, each of which is incorporated herein by reference.

In some embodiments, it may be desirable to remove all or a portion of the water from the green, shaped metal-carbon product in a drying step, prior to carrying out the carbonization step. Typically, the drying step is carried out either under ambient temperature (e.g., about 20° C.) and pressure, or at a temperature in the range of from about 20° C. to about 175° C., from about 20° C. to about 150° C., from about 40° C. to about 120° C., from about 60° C. to about 120° C., from about 90° C. to about 175° C., from about 90° C. to about 150° C., from about 100° C. to about 150° C., or from about 100° C. to about 140° C. The drying step may be carried out under a vacuum or otherwise reduced pressure, relative to ambient pressure. Methods for drying the green, shaped carbon product that are suitable for use in the processes of the present invention include those described in published PCT application WO 2015/168327, as well as U.S. applications U.S. Ser. No. 62/247,721 and U.S. Ser. No. 15/131,829 for drying a shaped carbon composite, each of which is incorporated herein by reference.

The carbonization step is typically conducted by heating the green, shaped metal-carbon product to a temperature in the range of from about 250° C. to about 1,000° C., from about 300° C. to about 900° C., from about 300° C. to about 850° C., from about 300° C. to about 800° C., from about 350° C. to about 850° C., from about 350° C. to about 800° C., from about 350° C. to about 700° C., from about 400° C. to about 850° C. or from about 400° C. to about 800° C. Suitable methods for carbonizing the green, shaped metal-carbon product include those described in. published PCT application WO 2015/168327, as well as U.S. applications U.S. Ser. No. 62/247,721 and U.S. Ser. No. 15/131,829 for carbonizing shaped carbon composites, each of which is incorporated herein by reference. The carbonization step, inter alia, renders the water-soluble organic binder, water-insoluble.

The processes described herein advantageously allow for the incorporation of a wide variety of metal species into a porous, yet durable carbon-based material. Exemplary porous shaped metal-carbon products include, for example, porous, shaped Ni-carbon products; porous shaped W-carbon products; porous shaped Co-carbon products; and the like, as well as such products having a further metal deposited thereon (on internal and external surfaces). As used herein, when a specific metal is recited as the "metal" or "metal component" with reference to the metal-carbon product, what is being referred to is the metal corresponding to the metal precursor compound, where such metal resides on and/or in the porous shaped metal-carbon product after the carbonization step. Without wishing to be bound by any theory, it is believed that in situ carbonization of the metal precursor within the metal-carbon mixture may impact the distribution of metal in/on the porous, shaped metal-carbon product, as compared to the distribution of metal in/on a corresponding control product. The "corresponding control product" in this case being prepared from a green, shaped carbon product that does not have metal incorporated in it, but has metal added to it post-carbonization (e.g., by impregnation) The difference may be potentially more pronounced with the use of a water-insoluble metal precursor in the processes of the present invention.

Without wishing to be bound by theory, it is believed that carbonization of the metal-carbon mixture may also alter the textural properties (e.g., surface area and porosity) of the carbonized product, as compared to product from carbonization of the green product without the metal incorporated. When a porous, shaped tungsten (W)-carbon product was prepared, the BET surface area was observed to be higher than a corresponding shaped carbon product prepared without the tungsten. Likewise, the BJH specific pore volume was lower in the W-carbon product of the present invention, as compared to without it. Furthermore, the average pore diameter was relatively larger in the W-carbon product of the present invention as compared to a corresponding shaped carbon product prepared without the tungsten.

The processes of the present invention provide further advantages. For example, when the metal precursor is capable of being decomposed and reduced to a metal at the carbonization temperature (i.e., in situ reduction), a further reduction step may be avoided. Such a process is attractive economically. In various embodiments, however, it may be desired to reduce the metal in the shaped metal-carbon product by contacting the product with a reducing agent, such as, for example, hydrogen (e.g., by flowing 5% $H_2$ in $N_2$ at 350° C. for 3 hours). Reduction of the shaped metal-carbon product is illustrated in the Examples.

The metal component of the porous, shaped metal-carbon product is typically present at a metal loading in the range of from about 0.1 wt % to about 50 wt %, from about 0.1 wt % to about 45 wt %, from 0.1 wt % to about 40 wt %, from about 0.1 wt % to about 35 wt %, from about 0.1 wt % to about 30 wt %, or from about 0.1 wt % to about 25 wt % of the total weight of the porous shaped metal-carbon product. In some embodiments, the metal loading is in the range of from about 0.5 wt % to about 50 wt %, from about 1 wt % to about 50 wt %, from about 1 wt % to about 45 wt %, from about 1 wt % to about 40 wt %, from about 1 wt % to about 35 wt %, from about 1 wt % to about 30 wt %, from about 1 wt % to about 25 wt %, or from about 1 wt % to about 20 wt % of the total weight of the porous shaped metal-carbon product.

The carbonized, shaped metal-carbon product typically has a carbon content in the range of from about 50 wt % to about 99.9 wt %. More typically, the carbon content is in the range of from about 55 wt % to about 99 wt %, from about 60 wt % to about 99 wt %, from about 65 wt % to about 99 wt %, from about 70 wt % to about 99 wt %, or from about 75 wt % to about 99 wt % of the total weight of the porous shaped metal-carbon product. Carbon content of the shaped metal-carbon product is determined by the following formula: [(Weight of carbonaceous material used to prepare the metal-carbon mixture)/(Weight of the porous shaped metal-carbon product)]×100%.

When carbon black is utilized during preparation of the carbonized shaped metal-carbon product, the product is typically a mesopore-dense product having a high concentration of mesopores with diameters in the range of from about 10 nm to about 100 nm or from about 10 nm to about 50 nm. In some embodiments, at least about 50%, at least about 60%, at least about 70%, at least about 80%, or at least about 90% of the pore volume of these shaped metal-carbon products is attributable to pores having a pore diameter of from about 10 nm to about 100 nm as measured by the BJH method (on the basis of pores having a diameter of from 1.7 nm to 100 nm). The term "mesopore-dense metal-containing carbon-based materials" refers herein to metal-containing carbon-based materials prepared in accordance with the processes described herein where carbon black is employed as the carbonaceous material.

In certain mesopore-dense, carbonized, shaped metal-carbon products of the present invention, the contribution to pore volume of pores having a pore diameter in the range of from about 10 nm to about 100 nm (on the basis of pores having a diameter of from 1.7 nm to 100 nm) is from about 50% to about 95%, from about 50% to about 90%, from about 50% to about 80%, from about 60% to about 95%, from about 60% to about 90%, from about 60% to about 80%, from about 70% to about 95%, from about 70% to about 90%, from about 70% to about 80%, from about 80% to about 95%, or from about 80% to about 90% of the pore volume as measured by the BJH method (on the basis of pores having a diameter of from 1.7 nm to 100 nm). In other embodiments, the contribution to pore volume of pores having a pore diameter in the range of from about 10 nm to about 50 nm (on the basis of pores having a diameter of from 1.7 nm to 100 nm) is at least about 35%, at least about 40%, at least about 45%, or at least about 50% of the pore volume as measured by the BJH method (on the basis of pores having a diameter of from 1.7 nm to 100 nm).

Typically, these mesopore-dense, carbonized, shaped metal-carbon products possess a relatively low concentration of pores having a pore diameter less than 10 nm, less than 5 nm, or less than 3 nm. In certain embodiments, no more than about 10%, no more than about 5%, or no more than about 1% of the pore volume of these materials is less than 10 nm, less than 5 nm, or less than 3 nm, as measured by the BJH method (on the basis of pores having a diameter from 1.7 nm to 100 nm). In other embodiments, the contribution to pore volume of pores having a pore diameter that is less than 10 nm, less than 5, or less than 3 nm, is in the range of from about 0.1% to about 10%, from about 0.1% to about 5%, from about 0.1% to about 1%, from about 1% to about 10%, from about 0.1% to about 5%, from about 0.1% to about 1%, from about 1% to about 10%, or from about 1% to about 5%, as measured by the BJH method (on the basis of pores having a diameter from 1.7 nm to 100 nm).

In some embodiments, the mesopore-dense, carbonized, shaped metal-carbon products of the present invention have a pore size distribution with no observable peaks below 10 nm, and in some embodiments, no observable peaks below 5 nm. In these and other embodiments, the mesopore-dense, carbonized, shaped metal-carbon products have a pore size distribution with the peak of the distribution at a pore size diameter that is greater than about 5 nm, greater than about 7.5 nm, greater than about 10 nm, greater than about 12.5 nm, greater than about 15 nm, or greater than about 20 nm, and usually less than about 100 nm, less than about 90 nm, less than about 80 nm, or less than about 70 nm.

Mesopore-dense, carbonized, shaped metal-carbon products of the present invention typically have a BET specific surface area in the range of from about 20 $m^2/g$ to about 500 $m^2/g$. In some embodiments, the BET specific surface area is in the range of from about 20 $m^2/g$ to about 350 $m^2/g$, from about 20 $m^2/g$ to about 250 $m^2/g$, from about 20 $m^2/g$ to about 225 $m^2/g$, from about 20 $m^2/g$ to about 200 $m^2/g$ from about 20 $m^2/g$ to about 175 $m^2/g$, from about 20 $m^2/g$ to about 150 $m^2/g$, from about 20 $m^2/g$ to about 125 $m^2/g$, or from about 20 $m^2/g$ to about 100 $m^2/g$, from about 25 $m^2/g$ to about 500 $m^2/g$, from about 25 $m^2/g$ to about 350 $m^2/g$, from about 25 $m^2/g$ to about 250 $m^2/g$, from about 25 $m^2/g$ to about 225 $m^2/g$ to about 150 $m^2/g$, from about 25 $m^2/g$ to about 125 $m^2/g$, from about 25 $m^2/g$ to about 100 $m^2/g$, from about 30 $m^2/g$ to about 500 $m^2/g$, from about 30 $m^2/g$ to about 350 $m^2/g$ from about 30 $m^2/g$ to about 250 $m^2/g$, from about 30 $m^2/g$ to about 225 $m^2/g$, from about 30 $m^2/g$ to about 200 $m^2/g$, from about 30 $m^2/g$ to about 175 $m^2/g$, from about 30 $m^2/g$ to about 150 $m^2/g$, from about 30 $m^2/g$ to about 125 $m^2/g$, or from about 30 $m^2/g$ to about 100 $m^2/g$.

The specific pore volume of mesopore-dense, carbonized, shaped metal-carbon products prepared according to the processes described herein, are typically greater than about 0.1 $cm^3/g$, as measured by the BJH method (on the basis of pores having a diameter in the range of from 1.7 nm to 100 nm). More typically the specific pore volume of the mesopore-dense, shaped metal-carbon products is greater than about 0.2 $cm^3/g$ or greater than 0.3 $cm^3/g$, as measured by the BJH method (on the basis of pores having a diameter in the range of from 1.7 nm to 100 nm). In some embodiments, the mesopore-dense, carbonized, shaped metal-carbon product of the present invention have a specific pore volume of pores having a diameter in the range of from 1.7 nm to 100 nm, as measured by the BJH method, that is from about 0.1 $cm^3/g$ to about 1.5 $cm^3/g$, from about 0.1 $cm^3/g$ to about 0.9 $cm^3/g$, from about 0.1 $cm^3/g$ to about 0.8 $cm^3/g$, from about 0.1 $cm^3/g$ to about 0.7 $cm^3/g$, from about 0.1 $cm^3/g$ to about 0.6 $cm^3/g$, from about 0.1 $cm^3/g$ to about 0.5 $cm^3/g$ from about 0.2 $cm^3/g$ to about 0.8 $cm^3/g$, from about 0.2 $cm^3/g$ to about 0.7 $cm^3/g$, from about 0.2 $cm^3/g$ to about 0.6 $cm^3/g$, from about 0.2 $cm^3/g$ to about 0.5 $cm^3/g$, from about 0.3 $cm^3/g$ to about 1 $cm^3/g$, from about 0.3 $cm^3/g$ to about 0.9 $cm^3/g$, from about 0.3 $cm^3/g$ to about 0.8 $cm^3/g$ to about 1 $cm^3/g$, from about 0.3 $cm^3/g$ to about 0.9 $cm^3/g$, from about 0.3 $cm^3/g$ to about 0.8 $cm^3/g$, from about 0.3 $cm^3/g$ to about 0.7 $cm^3/g$, from about 0.3 $cm^3/g$ to about 0.6 $cm^3/g$, or from about 0.3 $cm^3/g$ to about 0.5 $cm^3/g$.

Mesopore-dense, carbonized, shaped metal-carbon products of the present invention typically exhibit relatively high mechanical strength, and stability, particularly under aqueous conditions. In some embodiments, these materials comprise a radial piece crush strength of greater than about 4.4 N/mm (1 lb/mm). In other embodiments the mesopore-dense, carbonized, shaped metal-carbon products comprise a radial piece crush strength of greater than about 8.8 N/mm (2 lbs/mm), or greater than about 13.3 N/mm (3 lbs/mm). In certain embodiments, the radial piece crush strength of the mesopore-dense, carbonized, shaped metal-carbon product of the present invention is in the range of from about 4.4 N/mm (1 lb/mm) to about 88 N/mm (20 lbs/mm), from about 4.4 N/mm (1 lb/mm) to about 66 N/mm (15 lbs/mm), or from about 8.8 N/mm (1 lb/mm) to about 44 N/mm (10 lbs/mm). As used herein, the term "radial piece crush strength" refers to the piece crush strength test protocols described in ASTM D4179 or ASTM D6175, which are incorporated herein by reference. Though some of the test methods limit the particles to a defined dimensional range, geometry, or method of manufacture, crush strength of irregularly shaped particles and particles of varying dimension and manufacture may nevertheless be adequately measured by these and similar test methods.

In some embodiments, mesopore-dense, carbonized, shaped metal-carbon products prepared in accordance with the processes described herein exhibit attrition resistance and abrasion resistance characteristics. In these embodiments, the mesopore-dense, carbonized, shaped metal-carbon products (which for the purposes of this determination, is prepared in the form of an extrudate) typically exhibit a rotating drum attrition index, as measured in accordance with ASTM D4058-96, of greater than at least about 85 wt % retained on a 20-mesh sieve after a period of continuous rotation in the rotating test cylinder at 55 RPMs for 35 minutes. In certain embodiments, these materials exhibit a rotating drum attrition index of greater than at least about 90 wt %, greater than about 91 wt %, greater than about 92 wt %, greater than about 93 wt %, greater than about 94 wt %, greater than about 95 wt %, greater than about 96 wt %, greater than about 97 wt %, greater than about 98 wt %, or greater than about 99 wt % retained on a 20-mesh sieve in the above-described attrition test method.

Mesopore-dense, carbonized, shaped metal-carbon products of the present invention typically exhibit minimal abrasion loss after a duration of intense horizontal agitation. As used herein, the term "abrasion loss" refers to a measurement of the resistance of a material to attrition wear due to intense horizontal agitation of particles within the confines of a 30-mesh sieve. The material is tested as follows: (1) the material to be tested is first de-dusted on a 20-mesh sieve by gently moving the sieve side-to-side at least 20 times; (2) the de-dusted sample is weighed and then transferred to the inside of a clean, 30-mesh sieve stacked above a clean sieve pan for the collection of fines; (3) the completed sieve stack is then assembled onto a sieve shaker (e.g., RO-Tap RX-29 sieve shaker from W. S. Tyler Industrial Group, Mentor, Ohio), covered securely and shaken for about 30 minutes; (4) the collected fines generated are weighed; and (5) percent abrasion loss by weight is calculated by dividing the weight of collected fines by the de-dusted sample weight. In some embodiments, the mesopore-dense, carbonized, shaped metal-carbon products of the present invention exhibits a horizontal agitation sieve abrasion loss of less than about 5%, less than about 3%, less than about 2%, less than about 1%, less than about 0.5%, less than about 0.2%, less than about 0.1%, less than about 0.05%, or less than about 0.03%.

In certain applications, a relatively high surface area, shaped metal-carbon product may be desired, i.e., having a BET specific surface area of greater than about 500 $m^2/g$. The term "high surface area, shaped metal-carbon product" is used herein to refer to a shaped metal-carbon product prepared according to the methods of the present invention where the carbonaceous material is an activated carbon. High surface area, shaped metal-carbon products of the present invention typically exhibit a BET specific surface area that is greater than 500 $m^2/g$. In some embodiments, the BET specific area of these materials is in the range of from about 550 $m^2/g$ to about 3500 $m^2/g$. In certain embodiments, the BET specific surface area of these high surface materials is in the range of from about 600 $m^2/g$ to about 2500 $m^2/g$, from about 600 $m^2/g$ to about 2250 $m^2/g$, from about 600 $m^2/g$ to about 2000 $m^2/g$, or from about 700 $m^2/g$ to about 2000 $m^2/g$. In other embodiments, the BET specific surface are of the high surface area, carbonized, shaped metal-carbon products is in the range of from about 800 $m^2/g$ to about 2500 $m^2/g$, from about 800 $m^2/g$ to about 2000 $m^2/g$, or from about 1000 $m^2/g$ to about 2000 $m^2/g$.

High surface area, shaped metal-carbon products of the present invention typically possess higher concentrations of pores having a pore diameter less than 10 nm than the mesopore-dense, carbonized, shaped metal-carbon products described herein. Typically, the contribution to pore volume of pores having a pore diameter that is less than 10 nm, is greater than 10%, greater than about 20%, or greater than about 25%, as measured by the BJH method (on the basis of pores having a diameter from 1.7 nm to 100 nm).

In some embodiments, it may be desirable to employ graphite as the carbonaceous material in the preparation of the products of the present invention when, for example, improved electrical conductivity is desired. When graphite alone is employed as the carbonaceous material, the shaped metal-carbon products typically have a BET specific surface area of less than 20 $m^2/g$. However, as described above, mixtures of graphite with carbon black and/or activated carbon can be utilized in the metal-carbon mixture to tailor the porosity for the desired application.

The porous shaped metal-carbon products of the present invention may be thermally or chemically treated to modify its physical and/or chemical characteristics. For example, the products may be chemically treated with an oxidant to produce a more hydrophilic surface. In some embodiments, the porous shaped metal-carbon product may be surface-treated using known methods, to attach a desired functional group onto the surfaces of the material. See, e.g., WO 2002/018929, WO 97/47691, WO99/23174, and WO99/31175, which are incorporated herein by reference.

In certain embodiments, it may be desired to deposit additional metal onto the surfaces of the porous, shaped metal-carbon products of the present invention (including both internal pore surfaces, and exterior surfaces of the material), such as for use in certain catalytic applications. In these embodiments, a second metal (or precursor thereof) is deposited onto the surfaces of the porous shaped metal-carbon products of the present invention, where the second metal comprises a metal that is the same as or different from the metal in the first metal precursor (i.e., the metal precursor incorporated into the metal-carbon mixture).

For catalytic applications, the second metal and metal precursor can be any metal/metal precursor known to be useful in catalytic applications/catalyst manufacture. The second metal or precursor thereof can comprise a base metal or a noble metal. In some embodiments, the second metal or precursor thereof comprises a metal selected from groups IV, V, VI, VII, VIII, IX, X, XI, XII, and XIII. In various embodiments, the metal is a d-block metal. Exemplary d-block metals include, for example, Ni, Co, W, Cu, Zn, Fe, Mo, Ni, Rh, Pd, Ag, Os, Ir, Pt, Au, and the like.

In other embodiments, the second metal or precursor thereof comprises a metal selected from the group consisting of Cu, Pb, Ni, Zn, Fe, Mo, Al, Sn, W, Ta, Co, Bi, Cd, Ti, Zr, Sb, Mn, Be, Cr, Ge, V, Ga, Hf, In, Nb, Rh, Tl, Ru, Rh, Pd, Ag, Os, Ir, Pt, or Au. Often, the second metal is a noble metal. In specific embodiments, the second metal or precursor thereof comprises a metal selected from the group consisting of Cu, Pb, Ni, Zn, Fe, Mo, Al, Sn, W, Ta, Co, Bi, Cd, Ti, Zr, Sb, Mn, Be, Cr, Ge, V, Ga, Hf, In, Nb, Rh, and Tl.

In this step, the shaped metal-carbon product is typically contacted with a solubilized metal precursor in a liquid medium using a known method, such as, for example, incipient wetness, ion-exchange, deposition-precipitation, coating, vacuum impregnation, and the like. In some embodiments, following deposition of the second metal, the resulting material is optionally dried, for example at a temperature of at least about 50° C., more typically, at least about 120° C. for a period of time, that is typically at least about one hour, more typically, at least about three hours or more. Alternatively, the drying may be conducted in a continuous or staged manner where independently controlled temperature zones (e.g., 60° C., 80° C., and 120° C.) are utilized. Typically, drying is initiated by raising the temperature of the wet material to a temperature initially below the boiling point of the liquid medium, then increasing the temperature.

Following deposition and optional drying, the resulting product is heated in the presence of a reducing agent, such as, for example, hydrogen (e.g., a forming gas of 5% $H_2$ and 95% $N_2$), to reduce the metal precursor to the metal. The temperature at which the heating is conducted is typically in the range of from about 150° C. to about 600° C., from about 200° C. to about 500° C., or from about 100° C. to about 400° C. Heating is typically conducted for a period of time in the range of from about 1 hour to about 5 hours or from about 2 hours to about 4 hours. Reduction may also be carried out in the liquid phase. For example, metal deposition on the porous shaped metal-carbon product can be carried out in a fixed bed with liquid containing a reducing agent pumped through the static composite material. In some embodiments, the resulting catalyst material is calcined, for example, at a temperature of at least about 200° C. for a period of time (e.g., at least about one, two, or three hours). The deposition of a second metal onto the surfaces of the shaped metal-carbon product, followed by drying, reduction, and depleted air calcination is illustrated in Example 7.

In some embodiments, the surface-deposited metal(s) are present in the range of from about 0.1% to about 50%, from about 0.1% to about 25%, from about 0.1% to about 10%, from about 0.1% to about 5%, from about 0.25% to about 50%, from about 0.25% to about 25%, from about 0.25% to about 10%, from about 0.25% to about 5%, from about 1% to about 50%, from about 1% to about 25%, from about 1% to about 10%, from about 1% to about 5%, from about 5% to about 50% from about 5% to about 25% or from about 5% to about 10%, by weight of the porous, carbonized, shaped metal-carbon product. When the surface-deposited metal is a noble metal, it is typically present in a quantity in the range of from about 0.25 wt % to about 10 wt %. When the surface-deposited metal is a non-noble metal, it is often present in a quantity in the range of from about 0.1% to about 50 wt %.

The porous, shaped metal-carbon products of the present invention are particularly useful as catalysts. The type of catalytic activity can be customized for a particular reaction by changing the type of metal used in the metal precursor as demonstrated in the Examples. In some embodiments, the catalytic activity is a hydrogenation activity, a deoxyhydrogenation activity, an oxidation activity, a reduction activity, a dehydration activity, or other known catalytic activity using known active metals which can be conducted in either a gaseous or liquid medium. The porous shaped metal-carbon products may be employed as catalysts in batch, semi-batch or continuous reactor formats that are known in the art, such as, for example, fixed bed reactors, trickle bed reactors, slurry phase reactors, moving bed reactors, and the like. The products are suitable for use in either gaseous or liquid phase reactions. The porous shaped metal-carbon products are compatible with a wide range of solvents, including organic solvents, as well as water, and combinations thereof. Suitable compatible solvents include, for example, alcohols, such as, for example, ethanol, n-propanol, isopropanol, n-butanol, t-butanol, iso-butanol, sec-butanol, and the like; esters, such as, for example, methyl acetate, ethyl acetate, propyl acetate, butyl acetate, and the like; ethers, such as, for example, dioxane, glyme, diglyme, triglyme, tetraglyme, and the like; water; and mixtures thereof.

In one embodiment, the present invention provides a process for producing 2,5-bis-hydroxymethylfuran (BHMF) from 5-hydroxymethylfurfural (HMF), the method comprising:

contacting HMF with hydrogen in the presence of a hydrogenation catalyst comprising a porous, shaped metal-carbon product of the present invention to form BHMF, wherein the metal component of the porous, shaped metal-carbon product is selected from the group consisting of Ni, Zn, Co, Cu, Ag, Pt, Pd, Fe, Ru, Au, W, Sb, Bi, Pb, and combinations thereof. In some embodiments, the metal component of the porous shaped metal-carbon product is a combination of metals selected from the group consisting of Co/Cu, Ni/Cu, Ag/Ni, Ag/Co and Ag/Ru. Typically, the metal component of the porous shaped metal-carbon product of the present invention is a metal selected from the group consisting of Ni, Cu, and mixtures thereof.

The porous, shaped metal-carbon product typically comprises the metal component at a loading in the range of from about 0.5 wt % to about 99 wt %. In some embodiments, the loading is in the range of from about 0.1 wt % to about 25 wt %, or in the range of from about 0.1 wt % to about 20 wt %, or in the range of from about 0.1 wt % to about 18 wt %. When the porous, shaped metal-carbon product comprises two different species of metal components, M1 and M2, the molar ratio of metal 1 to metal 2 (M1:M2) is typically in the range of from about 25:1 to about 1:25 or from about 25:1 to about 2:1 or from about 20:1 to about 5:1.

The contacting step is typically carried out at a temperature in the range of from about 50° C. to about 150° C., or from about 80° C. to about 130° C. In one embodiment, the hydrogen pressure during the contacting step is in the range of from about 50 psig to about 2000 psig. In another embodiment, the hydrogen pressure is in the range of from about 100 psig to about 1500 psig. In a further embodiment, the hydrogen pressure is in the range of from about 200 psig to about 1000 psig.

The contacting step is typically carried out in an organic solvent, such as, for example, an alcohol, an ester, an ether, or a mixture thereof. Exemplary alcohols include, for example, ethanol, n-propanol, isopropanol, n-butanol, t-butanol, iso-butanol, sec-butanol, and the like. Exemplary esters include, for example, methyl acetate, ethyl acetate, propyl acetate, butyl acetate, and the like. Exemplary ethers include, for example, dioxane, dioxolane, glyme, diglyme, triglyme and tetraglyme. In one embodiment, the organic solvent contains less than about 25 wt % water. In another embodiment, the organic solvent contains less than about 10 wt % water. In another embodiment, the organic solvent contains less than about 5 wt % water. In another embodiment, the organic solvent is substantially free of water.

In one embodiment BHMF is generated from HMF with at least about 90% selectivity. In another embodiment, BHMF is generated from HMF with at least 95% selectivity. In some embodiments, BHMF is generated from HMF with at least 99% selectivity.

In some embodiments, at least about 85% of HMF is converted to BHMF. In certain embodiments, at least about 90% HMF is converted to BHMF. In other embodiments, at least 95% about HMF is converted to BHMF. In further embodiments, at least about 99% HMF is converted to BHMF.

In one embodiment, the present invention provides a process for producing bis-hydroxymethyltetrahydrofuran (BHMTHF) from 2,5-bis-hydroxymethylfuran (BHMF), the method comprising:

contacting BHMF with hydrogen in the presence of a heterogeneous hydrogenation catalyst comprising a porous shaped metal-carbon product of the present invention to form BHMTHF, wherein the metal component of the metal-carbon product is selected from the group consisting of Ni, Co, Cu, Ag, Pd, Pt, Ru, and combinations thereof. In some embodiments, the metal component is selected from the group consisting of Ni, Co, Pd, Ru, and Pt. In certain embodiments, the metal component is selected from the group consisting of Ni, Pd, Co, and Pt. In other embodiments, the metal component is a combination of metals, such as a combination selected from the group consisting of Co and Cu; Ni and Cu, Ru and Cu; Ag and Ni; Ag and Co; Ag and Ru; and Cu, Co, and Ni. Typically, the metal component is Ni.

The porous shaped metal-carbon product typically comprises the metal component at a loading in the range of from about 0.5 wt % to about 99 wt %. In some embodiments, the loading is in the range of from about 0.01 wt % to about 25 wt %, or in the range of from about 0.1 wt % to about 20 wt %, or in the range of from about 0.1 wt % to about 18 wt %. When the composite comprises two different metal species, M1 and M2, the molar ratio of metal 1 to metal 2 (M1:M2) is typically in the range of from about 25:1 to about 1:25 or from about 25:1 to about 2:1 or from about 20:1 to about 5:1.

The contacting step is typically carried out at a temperature in the range of from about 80° C. to about 150° C., or from about 80° C. to about 130° C. In one embodiment, the hydrogen pressure during the contacting step is in the range of from about 50 psig to about 2000 psig. In another embodiment, the hydrogen pressure is in the range of from about 100 psig to about 1500 psig. In a further embodiment, the hydrogen pressure is in the range of from about 200 psig to about 1000 psig.

The contacting step is typically carried out in an organic solvent, such as, for example, an alcohol, an ester, an ether, or a mixture thereof. Exemplary alcohols include, for example, ethanol, n-propanol, isopropanol, n-butanol, t-butanol, iso-butanol, sec-butanol, and the like. Exemplary esters include, for example, methyl acetate, ethyl acetate, propyl acetate, butyl acetate, and the like. Exemplary ethers include, for example, dioxane, dioxolane, glyme, diglyme, triglyme and tetraglyme. In one embodiment, the organic solvent contains less than about 25 wt % water. In one embodiment, the organic solvent is a mixture of 90% organic solvent and 10% water (v/v). In another embodiment, the organic solvent contains less than about 10 wt % water. In another embodiment, the organic solvent contains less than about 5 wt % water. In another embodiment, the organic solvent is substantially free of water.

In one embodiment BHMTHF is generated from BHMF with at least about 80% selectivity. In some embodiments BHMTHF is generated from BHMF with at least about 85% or at least about 90% selectivity. In another embodiment, BHMTHF is generated from BHMF with at least about 95% selectivity. In some embodiments, BHMTHF is generated from BHMF with at least 99% selectivity.

In some embodiments, at least about 85% of BHMF is converted to BHMTHF. In certain embodiments, at least about 90% BHMF is converted to BHMTHF. In other embodiments, at least 95% about BHMF is converted to BHMTHF. In further embodiments, at least about 99% BHMF is converted to BHMTHF. The conversion of BHMF to BHMTHF using a heterogeneous hydrogenation catalyst that is a porous, shaped Ni-carbon product is illustrated in Example 5.

In another embodiment, the present invention provides a process for producing a $C_3$-$C_6$ diol from a corresponding $C_3$-$C_6$ polyol, the method comprising:

contacting a $C_3$-$C_6$ polyol with hydrogen in the presence of a hydrodeoxygenation catalyst comprising a porous, shaped metal-carbon product of the present invention to form a corresponding $C_3$-$C_6$ diol, wherein the metal component of the porous, shaped metal-carbon product is a metal selected from the group consisting of Pd, Pt, Ir, Mo, W, V, Mn, Re, Zr, Ni, Cu, La, Sm, Y, Zn, Cr, Ge, Sn, Ti, Au, Rh, Co, and combinations thereof. In some embodiments, the metal component is selected from the group consisting of Pt, W, and Mo. In certain embodiments, the metal is selected from the group consisting of Pt and W. In other embodiments, the metal is W.

The porous, shaped metal-carbon products typically comprises the metal component at a loading in the range of from about 0.5 wt % to about 10 wt %. In some embodiments, the loading is in the range of from about 0.2 wt % to about 10 wt %, or in the range of from about 0.2 wt % to about 8 wt %, or in the range of from about 0.2 wt % to about 5 wt %. In some embodiments, the total weight of the metal component is less than about 4 wt % of the total weight of the porous, shaped metal-carbon product. When the product comprises two different species of metal components, M1 and M2, the molar ratio of metal 1 to metal 2 (M1:M2) is typically in the range of from about 20:1 to about 1:10 or from about 10:1 to about 1:5 or from about 8:1 to about 1:2.

In some embodiments, the $C_3$-$C_6$ diol is selected from the group consisting of 1,5-pentanediol and 1,6-hexanediol. The $C_3$-$C_6$ diol may be produced directly, or indirectly via one or more intermediates, from a $C_3$-$C_6$ polyol that is selected from the group consisting of 1,2,6-hexanetriol, 1,2,5-pentanetriol, 2H-tetrahydropyran-2-methanol, tetrahydrofuran-2,5-dimethanol, furan-2,5-dimethanol, 2,5-dihydrofuran-2,5-dimethanol, levoglucosenone, levoglucosan, levoglucosenol, 1,6-anhydro-3,4-dideoxy-p-D-pyranose-2-one, isosorbide, hydroxymethylfurfural, sorbitol, glucose, fructose, xylitol, 3,4-dihydro-2H-pyran-2-carbaldehyde, 1,2,5,6-hexanetetraol, 1,2,3,5,6-hexanepentanol, 1,5-anhydro-3,4-dideoxyhexitol, 5-hydroxy-2H-tetrahydropyran-2 methanol, furfural, furfuryl alcohol, tetrahydrofurfuryl alcohol, a pentose, NS a hexose. Indirect production of the $C_3$-$C_6$ diol may occur via an intermediate, such as, for example, furan dimethanol, tetrahydrofuran dimethanol, tetrahydropyran-2-methanol, levoglucosanol, furfuryl alcohol, and the like.

The conversion of the C3-C6 polyol to the corresponding C3-C6 diol can be conducted in the presence of a solvent. Solvents suitable for use in conjunction with the conversion of the C3-C6 polyol to the corresponding C3-C6 diol in the presence of the catalysts of the present invention include, for example, eater, alcohols, esters, ethers, ketones, or mixtures thereof. In various embodiments, the preferred solvent is water.

In an exemplary process, the $C_3$-$C_6$ polyol is 1,2,6-hexanetriol (HTO) and the $C_3$-$C_6$ diol is 1,6-hexanediol (HDO). Typically, metal component of the porous shaped metal-carbon product is a metal selected from the group consisting of Mo, W, and a mixture thereof. More typically, the porous, shaped metal-carbon product has a second metal deposited thereon (on the internal and external surfaces). Typically, the shaped metal-carbon product is a porous shaped W-carbon product having platinum deposited thereon (on the internal and external surfaces).

In one embodiment, the contacting step is carried out at a temperature in the range of from about 80° C. to about 200°

C. In another embodiment, the contacting step is carried out at a temperature in the range of from about 100° C. to about 180° C. Typically, the hydrogen pressure during the contact step is in the range of from about 200 psig to about 5000 psig, in the range of from about 200 psig to about 4000 psig, in the range of from about 200 psig or 500 psig to about 3000 psig. In other embodiments the hydrogen pressure is in the range of from about 200 psig or 500 psig to about 2000 psig.

In one embodiment, the desired $C_3$-$C_6$ diol is generated from the $C_3$-$C_6$ diol with at least about 80% selectivity. In another embodiment, the desired $C_3$-$C_6$ diol is generated from the $C_3$-$C_6$ diol with at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% selectivity. In some embodiments, at least about 25% of the $C_3$-$C_6$ polyol is converted to the desired $C_3$-$C_6$ diol. In certain embodiments, at least about 30% of the $C_3$-$C_6$ polyol is converted to the desired $C_3$-$C_6$ diol. In other embodiments, at least about 35%, at least about 40%, at least about 45%, at least about 50%, at least about 55%, at least about 60%, at least bout 65%, at least about 70%, at least about 75%, at least about 80%, at least about 85%, at least about 90%, or at least about 95% of the $C_3$-$C_6$ polyol is converted to the desired $C_3$-$C_6$ diol. In a specific embodiment, the $C_3$-$C_6$ polyol is 1,2,6-hexanetriol and the $C_3$-$C_6$ diol is 1,6-hexanediol.

In another embodiment, the present invention provides a process for the selective amination of 1,6-hexanediol (HDO) to 1,6-hexamethylenediamine (HMDA) comprising contacting the 1,6-hexanediol with an amine in the presence of an amination catalyst comprising a porous, shaped metal-carbon product of the present invention, wherein the metal component of the porous, shaped metal-carbon product is selected from the group consisting of Ni, Ru, and Rh. Typically, the metal component is Ni. In some embodiments of this process, Ru and/or Rh are deposited as a second metal (or mixture of metals) on the porous, shaped metal-carbon product. Typically, the total weight of metal(s) is from about 0.1% to about 10%, from about 1% to about 6%, or from about 1% to about 5% of the total weight of the catalyst composition.

In this process, when both Ru and Rh are employed, the molar ratio of Ru to Rh is important. A by-product of processes for converting HDO to HMDA is pentylamine. Pentylamine is an off path by-product of the conversion of HDO to HMDA that cannot be converted to HMDA or to an intermediate which can, on further reaction in the presence of the catalysts of the present invention, be converted to HMDA. However, the presence of too much rhodium can have an adverse effect on the yield of HMDA per unit area time (commonly known as space time yield, or STY). Therefore, the molar ratio of Ru:Rh should be maintained in the range of from about 20:1 to about 4:1. In various embodiments, the Ru:Rh molar ratio is in the range of from about 10:1 to about 4:1 or from about 8:1 to about 4:1. In some embodiments, the Ru:Rh molar ratio of from about 8:1 to about 4:1 produces HMDA in at least 25% yield with an HMDA/pentylamine ratio of at least 20:1, at least 25:1, or at least 30:1.

In accordance with the present invention, HDO is converted to HMDA by reacting HDO with an amine, e.g., ammonia, in the presence of the porous, shaped metal-carbon products of the present invention. Generally, in some embodiments, the amine may be added to the reaction in the form of a gas or liquid. Typically, the molar ratio of ammonia to HDO is at least about 40:1, at least about 30:1, or at least about 20:1. In various embodiments, it is in the range of from about 40:1 to about 5:1, from about 30:1 to about 10:1. The reaction of HDO with amine in the presence of the catalysts of the present invention is carried out at a temperature less than or equal to about 200° C. In various embodiments, the catalyst is contacted with HDO and amine at a temperature less than or equal to about 100° C. In some embodiments, the catalyst is contacted with HDO and amine at a temperature in the range of about 100° C. to about 180° C. or about 140° C. to about 180° C.

Generally, in accordance with the present invention, the reaction is conducted at a pressure not exceeding about 1500 psig. In various embodiments, the reaction pressure is in the range of about 200 psig to about 1500 psig. In other embodiments, and a pressure in the range of about 400 psig to about 1200 psig. In certain preferred embodiments, the pressure in the range of about 400 psig to about 1000 psig. In some embodiments, the disclosed pressure ranges includes the pressure of $NH_3$ gas and an inert gas, such as $N_2$. In some embodiments, the pressure of $NH_3$ gas is in the range of about 50-150 psig and an inert gas, such as $N_2$ is in the range of about 700 psig to about 1450 psig.

In some embodiments, the catalyst is contacted with HDO and ammonia at a temperature in the range of about 100° C. to about 180° C. and a pressure in the range of about 200 psig to about 1500 psig. In other embodiments, the catalyst is contacted with HDO and ammonia at a temperature in the range of about 140° C. to about 180° C. and a pressure in the range of about 400 psig to about 1200 psig. In some embodiments, the disclosed pressure ranges includes the pressure of $NH_3$ gas and an inert gas, such as $N_2$. In some embodiments, the pressure of $NH_3$ gas is in the range of about 50-150 psig and an inert gas, such as $N_2$ is in the range of about 500 psig to about 1450 psig.

The process of the present invention may be carried out in the presence of hydrogen. Typically, in those embodiments in which the HDO and amine are reacted in the presence of hydrogen and the catalyst of the present invention, the hydrogen partial pressure is equal to or less than about 100 psig.

The conversion of HDO to HMDA can also be conducted in the presence of a solvent. Solvents suitable for use in conjunction with the conversion of HDO to HMDA in the presence of the catalysts of the present invention may include, for example, water, alcohols, esters, ethers, ketones, or mixtures thereof. In various embodiments, the preferred solvent is water.

The chemocatalytic conversion of HDO to HMDA is likely to produce one or more by-products such as, for example, pentylamine and hexylamine. By-products which are subsequently convertible to HMDA by further reaction in the presence of catalysts of the present invention are considered on-path by-products. Other by-products such as, for example, pentylamine and hexylamine are considered off path by-products for the reasons above discussed. In accordance with the present invention, at least 20%, at least 30%, at least 40%, at least 50%, at least 60%, or at least 70% of the product mixture resulting from a single pass reaction of HDO with amine (e.g., ammonia) in the presence of the catalysts of the present invention is HMDA.

The resulting product mixture may be separated into one or more products by any suitable methods known in the art. In some embodiments, the product mixture can be separated by fractional distillation under subatmospheric pressures.

For example, in some embodiments, HMDA can be separated from the product mixture at a temperature between about 180° C. and about 220° C. The HDO may be recovered from any remaining other products of the reaction mixture by one or more conventional methods known in the art including, for example, solvent extraction, crystallization or evaporative processes. The on-path by-products can be recycled to the reactor employed to produce the product mixture or, for example, supplied to a second reactor in which the on path by-products are further reacted with ammonia in the presence of the catalysts of the present invention to produce additional HMDA.

One series of catalytic applications that the porous, shaped metal-carbon products of the present invention are suited for is the selective oxidation of a hydroxyl group to a carboxyl group in a liquid or gaseous reaction medium. An exemplary reaction is the selective oxidation of an aldose to an aldaric acid. Aldoses include, for example, pentoses and hexoses (i.e., C-5 and C-6 monosaccharides). Pentoses include ribose, arabinose, xylose, and lyxose, and hexoses include glucose, allose, altrose, mannose, gulose, idose, galactose, and talose. Accordingly, in various embodiments, the present invention is also directed to a process for the selective oxidation of an aldose to an aldaric acid comprising reacting the aldose with oxygen in the presence of an oxidation catalyst comprising a porous, shaped metal-carbon product of the present invention to form the aldaric acid. Typically, the porous, shaped metal-carbon product is a base metal-carbon product with a noble metal, e.g., platinum, deposited thereon (i.e., on external and internal surfaces). More typically, the nobel metal is a mixture of platinum and gold. Often the base metal component of the base metal-carbon product is tungsten.

In a specific embodiment, the present invention provides a process for the selective oxidation of glucose to glucaric acid comprising contacting the glucose with oxygen in the presence of an oxidation catalyst comprising a porous, shaped metal-carbon product as described herein to form glucaric acid. Typically, the porous, shaped metal-carbon product is a base metal-carbon product with a noble metal, e.g., platinum, deposited thereon (i.e., on external and internal surfaces). More typically, the nobel metal is a mixture of platinum and gold. Often the base metal component of the base metal-carbon product is tungsten. The conversion of glucose to glucaric acid using a Au—Pt on a porous, shaped W-carbon product is described in Example 14.

U.S. Pat. No. 8,669,397, the entire contents of which are incorporated herein by reference, discloses various catalytic processes for the oxidation of glucose to glucaric acid. In general, glucose may be converted to glucaric acid in high yield by reacting glucose with oxygen (e.g., air, oxygen-enriched air, oxygen alone, or oxygen with other constituents substantially inert to the reaction) in the presence of an oxidation catalyst according to the following reaction:

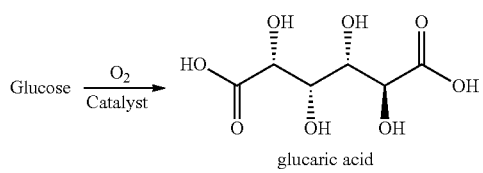 [SMILES: "O2" ; O=C(O)[C@@H](O)[C@@H](O)[C@H](O)[C@@H](O)C(=O)O]

glucaric acid

The oxidation can be conducted in the absence of added base (e.g., KOH) or where the initial pH of the reaction medium and/or the pH of reaction medium at any point in the reaction is no greater than about 7, no greater than 7.0, no greater than about 6.5, or no greater than about 6. The initial pH of the reaction mixture is the pH of the reaction mixture prior to contact with oxygen in the presence of an oxidation catalyst. In fact, catalytic selectivity can be maintained to attain glucaric acid yield in excess of about 30%, about 40%, about 50%, about 60% and, in some instances, attain yields in excess of 65% or higher. The absence of added base advantageously facilitates separation and isolation of the glucaric acid, thereby providing a process that is more amenable to industrial application, and improves overall process economics by eliminating a reaction constituent. The "absence of added base" as used herein means that base, if present (for example, as a constituent of a feedstock), is present in a concentration which has essentially no effect on the efficacy of the reaction; i.e., the oxidation reaction is being conducted essentially free of added base. The oxidation reaction can also be conducted in the presence of a weak carboxylic acid, such as acetic acid, in which glucose is soluble. The term "weak carboxylic acid" as used herein means any unsubstituted or substituted carboxylic acid having a pKa of at least about 3.5, more preferably at least about 4.5 and, more particularly, is selected from among unsubstituted acids such as acetic acid, propionic acid or butyric acid, or mixtures thereof.

The oxidation reaction may be conducted under increased oxygen partial pressures and/or higher oxidation reaction mixture temperatures, which tends to increase the yield of glucaric acid when the reaction is conducted in the absence of added base or at a pH below about 7.

Typically, the partial pressure of oxygen is at least about 15 pounds per square inch absolute (psia) (104 kPa), at least about 25 psia (172 kPa), at least about 40 psia (276 kPa), or at least about 60 psia (414 kPa). In various embodiments, the partial pressure of oxygen is up to about 1,000 psia (6895 kPa), more typically in the range of from about 15 psia (104 kPa) to about 500 psia (3447 kPa), from about 75 psia (517 kPa) to about 500 psia (3447 kPa), from about 100 psia (689 kPa) to about 500 psia (3447 kPa), from about 150 psia (1034 kPa) to about 500 psia (3447 kPa). Generally, the temperature of the oxidation reaction mixture is at least about 40° C., at least about 60° C., at least about 70° C., at least about 80° C., at least about 90° C., at least about 100° C., or higher. In various embodiments, the temperature of the oxidation reaction mixture is from about 40° C. to about 200° C., from about 60° C. to about 200° C., from about 70° C. to about 200° C., from about 80° C. to about 200° C., from about 80° C. to about 180° C., from about 80° C. to about 150° C., from about 90° C. to about 180° C., or from about 90° C. to about 150° C.

Oxidation of glucose to glucaric acid can also be conducted in the absence of nitrogen as an active reaction constituent. Some processes employ nitrogen compounds such as nitric acid as an oxidant. The use of nitrogen in a form in which it is an active reaction constituent, such as nitrate or nitric acid, results in the need for $NO_x$ abatement technology and acid regeneration technology, both of which add significant cost to the production of glucaric acid from these known processes, as well as providing a corrosive environment which may deleteriously affect the equipment used to carry out the process. By contrast, for example, in the event air or oxygen-enriched air is used in the oxidation reaction of the present invention as the source of oxygen, the nitrogen is essentially an inactive or inert constituent. Thus, an oxidation reaction employing air or oxygen-enriched air is a reaction conducted essentially free of nitrogen in a form in which it would be an active reaction constituent.

Suitable methods for depositing platinum and gold, including identification of appropriate precursors are described in U.S. Patent Application Publication 2011/0306790, which is incorporated herein by reference. This publication describes various oxidation catalysts comprising a catalytically active component comprising platinum and gold, which are useful for the selective oxidation of compositions comprised of a primary alcohol. When platinum is employed, typically the mass ratio of glucose to platinum is from about 10:1 to about 1000:1, from about 10:1 to about 500:1, from about 10:1 to about 200:1, or from about 10:1 to about 100:1.

In another series of chemical transformations that the porous, shaped metal-carbon products are suited for use as hydrodeoxygenation catalysts for the hydrodeoxygenation of carbon-hydroxyl groups to carbon-hydrogen groups in a liquid or gaseous reaction medium. For example, one series of chemical transformation that the catalyst compositions of the present invention are especially suited for is the selective halide-promoted hydrodeoxygenation of an aldaric acid or salt, ester, or lactone thereof to a dicarboxylic acid. Accordingly, porous, shaped metal-carbon products of the present invention as described herein can be utilized as hydrodeoxygenation catalysts. As such, the present invention is also directed to a process for the selective halide promoted hydrodeoxygenation of an aldaric acid comprising contacting the aldaric acid or salt, ester, or lactone thereof with hydrogen in the presence of a halogen-containing compound and a hydroxygenation catalyst comprising a porous, shaped metal-carbon product of the present invention to form a dicarboxylic acid. Typically, the porous, shaped metal-carbon product is a porous, shaped base metal-carbon product having at least one noble metal deposited thereon (on the exterior and interior surfaces). Typically, the noble metal is selected from the group consisting of Ru, Rh, Pd, Pt, Au, Ag, Os, Ir, and combinations thereof. The metal component of the porous, shaped metal-carbon product is typically a metal selected from the group consisting of Co, Ni, Ti, V, Cr, Mn, Fe, Cu, Mo, W, and combinations thereof.

The hydrodeoxygenation catalysts of the present invention may be employed in the selective halide-promoted hydrodeoxygenation of glucaric acid or salt, ester, or lactone thereof to adipic acid. U.S. Pat. No. 8,669,397, referenced above and incorporated herein by reference, describes the chemocatalytic processes for the hydrodeoxygenation of glucaric acid to adipic acid.

Adipic acid or salts and esters thereof may be prepared by reacting, in the presence of a hydrodeoxygenation catalyst and a halogen source, glucaric acid or salt, ester, or lactone thereof, and hydrogen, according to the following reaction:

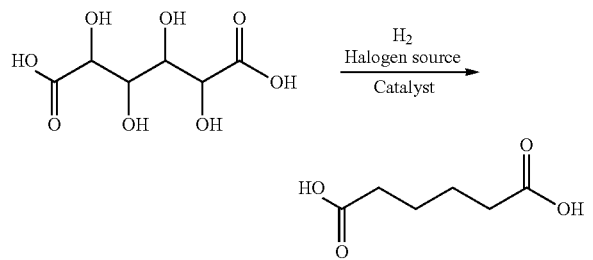

In the above reaction, glucaric acid or salt, ester, or lactone thereof is converted to an adipic acid product by catalytic hydrodeoxygenation in which carbon-hydroxyl groups are converted to carbon-hydrogen groups. In various embodiments, the catalytic hydrodeoxygenation is hydroxyl-selective wherein the reaction is completed without substantial conversion of the one or more other non-hydroxyl functional group of the substrate.

The halogen source may be in a form selected from the group consisting of ionic, molecular, and mixtures thereof. Halogen sources include hydrohalic acids (e.g., HCl, HBr, HI and mixtures thereof; preferably HBr and/or HI), halide salts, (substituted or unsubstituted) alkyl halides, or molecular (diatomic) halogens (e.g., chlorine, bromine, iodine or mixtures thereof; preferably bromine and/or iodine). In various embodiments the halogen source is in diatomic form, hydrohalic acid, or halide salt and, more preferably, diatomic form or hydrohalic acid. In certain embodiments, the halogen source is a hydrohalic acid, in particular hydrogen bromide.

Generally, the molar ratio of halogen to the glucaric acid or salt, ester, or lactone thereof is about equal to or less than about 1. In various embodiments, the mole ratio of halogen to the glucaric acid or salt, ester, or lactone thereof is typically from about 1:1 to about 0.1:1, more typically from about 0.7:1 to about 0.3:1, and still more typically about 0.5:1.

Generally, the reaction allows for recovery of the halogen source and catalytic quantities (where molar ratio of halogen to the glucaric acid or salt, ester, or lactone thereof is less than about 1) of halogen can be used, recovered and recycled for continued use as a halogen source.

Generally, the temperature of the hydrodeoxygenation reaction mixture is at least about 20° C., typically at least about 80° C., and more typically at least about 100° C. In various embodiments, the temperature of the hydrodeoxygenation reaction is conducted in the range of from about 20° C. to about 250° C., from about 80° C. to about 200° C., from about 120° C. to about 180° C., or from about 140° C. to 180° C. Typically, the partial pressure of hydrogen is at least about 25 psia (172 kPa), more typically at least about 200 psia (1379 kPa) or at least about 400 psia (2758 kPa). In various embodiments, the partial pressure of hydrogen is from about 25 psia (172 kPa) to about 2500 psia (17237 kPa), from about 200 psia (1379 kPa) to about 2000 psia (13790 kPa), or from about 400 psia (2758 kPa) to about 1500 psia (10343 kPa).

The hydrodeoxygenation reaction may be conducted in the presence of a solvent. Solvents suitable for the selective hydrodeoxygenation reaction include water and carboxylic acids, amides, esters, lactones, sulfoxides, sulfones and mixtures thereof. Preferred solvents include water, mixtures of water and weak carboxylic acid, and weak carboxylic acid. A preferred weak carboxylic acid is acetic acid.

Embodiments of the invention include the following:

1. A process for preparing a porous, shaped metal-carbon product, the process comprising:
mixing a carbonaceous material with water, a water-soluble organic binder, and a (first) metal precursor to form a metal-carbon mixture, wherein the metal precursor is a compound selected from the group consisting of a metal carbonate, a metal oxide, a metal hydroxide, a salt of a metal acid, a heteropoly acid, a metal carboxylate, hydrates thereof, and a mixture thereof;
shaping the metal-carbon mixture to form a green shaped metal-carbon product; and
heating the green shaped metal-carbon product to a carbonization temperature to produce a carbonized, shaped metal-carbon product comprising a plurality of pores.

2. The process of embodiment 1, wherein the metal precursor is a metal carbonate or hydrate thereof.

3. The process of embodiment 1, wherein the metal precursor is a metal oxide or hydrate thereof.

4. The process of embodiment 1, wherein the metal precursor is a metal hydroxide or hydrate thereof.

5. The process of embodiment 1, wherein the metal precursor is a salt of a metal acid or hydrate thereof.

6. The process of embodiment 1, wherein the metal precursor is a heteropoly acid or hydrate thereof.

7. The process of embodiment 1, wherein the metal precursor is a carboxylate of a metal acid or hydrate thereof.

8. The process of any of embodiments 1-7, wherein the metal precursor comprises a metal that is a base metal.

9. The process of any of embodiments 1-7, wherein the metal precursor comprises a metal selected from the group consisting of Cu, Pb, Ni, Zn, Fe, Mo, Al, Sn, W, Ta, Co, Bi, Cd, Ti, Zr, Sb, Mn, Be, Cr, Ge, V, Ga, Hf, In, Nb, Rh, Tl, Ru, Rh, Pd, Ag, Os, Ir, Pt, Au, and combinations thereof.

10. The process of embodiment 9, wherein the metal precursor comprises a metal selected from the group consisting of Cu, Pb, Ni, Zn, Fe, Mo, Al, Sn, W, Ta, Co, Bi, Cd, Ti, Zr, Sb, Mn, Be, Cr, Ge, V, Ga, Hf, In, Nb, Rh, Tl, and combinations thereof.

11. The process of embodiment 10, wherein the metal precursor comprises a metal selected from the group consisting of Ni, Co, W, Nb, Mo, and combinations thereof.

12. The process of any of embodiments 1-7, wherein the metal precursor is capable of being decomposed and reduced to a metal at a temperature in the range of from about 250° C. to about 1,000° C.

13. The process of any of embodiments 1-2 and 8-11, wherein the metal precursor is a nickel carbonate or hydrate thereof.

14. The process of any of embodiments 1, 5, and 8-11, wherein the metal precursor is ammonium metatungstate hydrate.

15. The process of any of embodiments 1-12, wherein the metal precursor is water insoluble.

16. The process of any of embodiments 1-12, wherein the metal precursor is water soluble.

17. The process of any of embodiments 1-16, wherein the metal precursor is present in the metal-carbon mixture in a quantity in the range of from about 0.1 wt % to about 90 wt %.

18. The process of embodiment 17, wherein the metal precursor is present in the metal-carbon mixture in a quantity in the range of from about 5 wt % to about 70 wt %.

19. The process of embodiment 18, wherein the metal precursor is present in the metal-carbon mixture in a quantity in the range of from about 10 wt % to about 70 wt %.

20. The process of embodiment 18, wherein the metal precursor is present in the metal-carbon mixture in a quantity in the range of from about 5 wt % to about 60 wt %.

21. The process of embodiment 18, wherein the metal precursor is present in the metal-carbon mixture in a quantity in the range of from about 10 wt % to about 60 wt %.

22. The process of embodiment 18, wherein the metal precursor is present in the metal-carbon mixture in a quantity in the range of from about 15 wt % to about 70 wt %.

23. The process of embodiment 22, wherein the metal precursor is present in the metal-carbon mixture in a quantity in the range of from about 25 wt % to about 60 wt %.

24. The process of embodiment 17, wherein the metal precursor is present in the metal-carbon mixture in a quantity in the range of from about 0.1 wt % to about 10 wt %.

25. The process of embodiment 24, wherein the metal precursor is present in the metal-carbon mixture in a quantity in the range of from about 0.1 wt % to about 5 wt %.

26. The process of embodiment 25, wherein the metal precursor is present in the metal-carbon mixture in a quantity in the range of from about 0.5 wt % to about 5 wt %.

27. The process of any of embodiments 1-26, wherein the carbonaceous material is present in the metal-carbon mixture in a quantity in the range of from about 15 wt % to about 80 wt %.

28. The process of embodiment 27, wherein the carbonaceous material is present in the metal-carbon mixture in a quantity in the range of from about 20 wt % to about 60 wt %.

29. The process of embodiment 27, wherein the carbonaceous material is present in the metal-carbon mixture in a quantity in the range of from about 15 wt % to about 35 wt %.

30. The process of any of embodiments 1-29, wherein the water-soluble organic binder and carbonaceous material are present in the metal-carbon mixture in a weight ratio of at least about 1:4, at least about 1:3, at least about 1:2 at least about 1:1, or at least about 1.5:1.

31. The process of any of embodiments 1-30, wherein the binder is present in the metal-carbon mixture in a quantity in the range of from about 10 wt % to about 50 wt %.

32. The process of any of embodiments 1-31, wherein the water is present in the metal-carbon mixture in a quantity that is not more than about 80% by weight of the metal-carbon mixture.

33. The process of any of embodiments 1-32, wherein the water-soluble organic binder is a water-soluble polymer.

34. The process of embodiment 33, wherein the water-soluble polymer is a carbohydrate.

35. The process of embodiment 34, wherein the carbohydrate is a cellulose.

36. The process of any of embodiments 1-22, wherein the water-soluble organic binder is a sugar.

37. The process of any of embodiments 1-32, wherein the organic water-soluble binder is a mixture of a cellulose and a sugar.

38. The process of any of embodiments 1-37, wherein the mixing step is carried out in a mixer selected from the group consisting of a mix muller, a planetary mixer, a drum mixer, a pan mixer, a twin shaft mixer, and a cement mixer.

39. The process of any of embodiments 1-38, further comprising premixing together a subset of components selected from the group consisting of the water, the water-soluble organic binder, the carbonaceous material, and the metal precursor.

40. The process of embodiment 39, comprising premixing together the water and the water-soluble organic binder to form a binder solution.

41. The process of embodiment 39, comprising premixing together the water, water-soluble organic binder, and the metal precursor.

42. The process of embodiment 39, further comprising premixing together the carbonaceous material and the metal precursor.

43. The process of any of embodiments 1-42 wherein the shaping step comprises a process selected from the group consisting of pressing, casting, injection molding, extruding, spreading, pelletizing, granulating, calandaring, and 3-D printing.

44. The process of embodiment 43, wherein the shaping step further comprises breaking the product of a process selected from the group consisting of pressing, casting, injection molding, extruding, spreading, pelletizing, granulating, calendering, and 3-D printing, into smaller pieces.

45. The process of any of embodiments 1-44 further comprising drying the metal-carbon mixture to remove at least a portion of the water prior to heating the green, shaped metal-carbon product to the carbonization temperature.

46. The process of embodiment 45, wherein the drying is carried out at a temperature in the range of from about 20° C. to about 150° C., or from about 40° C. to about 120° C., or from about 60° C. to about 120° C.

47. The process of any of embodiments 1-46, wherein the carbonization temperature is in the range of from about 250° C. to about 1000° C., or from about 300° C. to about 950° C., or from about 300° C. to about 900° C., or from about 350° C. to about 900° C., or from about 350° C. to about 850° C. or from about 350° C. to about 800° C.

48. The process of any of embodiments 1-47, further comprising contacting the carbonized, shaped metal-carbon product with a reducing agent at a temperature in the range of from about 100° C. to about 600° C.

49. The process of any of embodiments 1-48, further comprising forming particles of the carbonized, shaped metal-carbon product.

50. The process of any of embodiments 1-49, wherein the carbonized, shaped metal-carbon product comprises the metal in an amount in the range of from about 0.1 wt % to about 70 wt %.

51. The process of any of embodiments 1-50, wherein the carbonized, shaped metal-carbon product exhibits a catalytic activity.

52. The process of any of embodiments 1-51, wherein the carbonized, shaped metal-carbon product is electrically conductive.

53. The process of any of embodiments 1-52, wherein the carbonaceous material is a carbon black.

54. The process of any of embodiments 1-52, wherein the carbonaceous material is an activated carbon.

55. The process of any of embodiments 1-52, wherein the carbonaceous material is a graphite.

56. The process of any of embodiments 1-52, wherein the carbonaceous material is a mixture of any two or more materials selected from the group consisting of a carbon black, an activated carbon, and a graphite.

57. The process of any of embodiments 1-54 and 56, wherein the carbonaceous material has a BET specific surface area of at least about 20 m$^2$/g.

58. The process of embodiment 57, wherein the carbonaceous material has a BET specific surface area in the range of from about 20 m$^2$/g to about 500 m$^2$/g.

59. The process of any of embodiments 1-53 and 57-58, wherein the carbonized, shaped metal-carbon product comprises a pore volume, wherein from about 50% to about 95% of the pore volume is from pores having a pore diameter in the range of from about 5 nm to about 100 nm, as measured by the BJH process on the basis of pores having a diameter of from 1.7 nm to 100 nm.

60. The process of embodiment 1-53 and 57-59, wherein no more than about 10% of the pore volume is from pores having a pore diameter less than about 10 nm.

61. The process of any of embodiments 1-53 and 57-60, wherein the carbonized, shaped metal-carbon product comprises a specific pore volume of pores having a diameter in the range of from 1.7 nm to 100 nm, as measured by the BJH process, that is from about 0.1 cm$^3$/g to about 1.5 cm$^3$/g.

62. The process of any of embodiments 1-53 and 57-61, wherein the carbonized, shaped metal-carbon product exhibits a radial piece crush strength of greater than about 4.4 N/mm (1 lb/mm).

63. The process of any of embodiments 1-52 and 54, wherein the carbonaceous material has a BET specific surface area in the range of from about 550 m$^2$/g to about 3500 m$^2$/g.

64. The process of any of embodiments 1-63, further comprising depositing a second metal precursor on the surfaces of the carbonized, shaped metal-carbon product.

65. The process of embodiment 64, wherein the second metal precursor comprises a metal that is different from the metal in the first metal precursor.

66. The process of embodiment 65, wherein the second metal precursor comprises a metal that is a noble metal.

67. The carbonized, shaped metal-carbon product of any of embodiments 1-66.

68. A porous shaped metal-carbon product comprising a porous carbon matrix and a metal component, wherein the metal component of the porous, shaped metal-carbon product is present at a metal loading of at least about 10 wt %.

69. The porous shaped metal-carbon product of embodiment 68, wherein the metal loading is at least about 11 wt %, at least about 12 wt %, at least about 13 wt %, at least about 14 wt %, at least about 15 wt %, at least about 16 wt %, at least about 17 wt %, at least about 18 wt %, at least about 19 wt %, or at least about 20 wt %.

70. The product of any of embodiments 66-67, wherein the metal component of the porous, shaped metal-carbon product is a base metal.

71. The product of any of embodiments 68-70, wherein the metal component of the porous, shaped metal-carbon product is selected from the group consisting of Cu, Pb, Ni, Zn, Fe, Mo, Al, Sn, W, Ta, Co, Bi, Cd, Ti, Zr, Sb, Mn, Be, Cr, Ge, V, Ga, Hf, In, Nb, Rh, Tl, Ru, Rh, Pd, Ag, Os, Ir, Pt, Au, and combinations thereof.

72. The product of embodiment 71, wherein the metal component of the metal-carbon product is selected from the group consisting of Cu, Pb, Ni, Zn, Fe, Mo, Al, Sn, W, Ta, Co, Bi, Cd, Ti, Zr, Sb, Mn, Be, Cr, Ge, V, Ga, Hf, In, Nb, Rh, Tl, and combinations thereof.

73. The product of embodiment 72, wherein the metal component of the metal-carbon product is selected from the group consisting of Ni, Co, W, Nb, Mo, and combinations thereof.

74. The product of embodiment 73, wherein the metal component of the metal-carbon product is selected from the group consisting of Ni, W, and combinations thereof.

75. The product of any of embodiments 67-74, further comprising a second metal deposited on the surfaces of the porous shaped metal-carbon product.

76. The product of embodiment 75, wherein the second metal is different from the metal component of the metal-carbon product.

77. The porous shaped metal-carbon product of embodiment 76, wherein the second metal is a noble metal.

78. The porous shaped metal-carbon product of embodiment 77, wherein the noble metal is selected from the group consisting of Pt and Au.

79. The porous shaped metal-carbon product of any of embodiments 67-78, wherein the product is catalytically active.

80. A process for producing bis-hydroxymethyltetrahydrofuran (BHMTHF) from 2,5-bis-hydroxymethylfuran (BHMF), the process comprising:

contacting BHMF with hydrogen in the presence of a heterogeneous hydrogenation catalyst comprising a porous shaped metal-carbon product to form BHMTHF, wherein the metal component of the metal-carbon product is selected from the group consisting of a Ni, Co, Cu, Ag, Pd, Pt, Ru, and combinations thereof.

81. The process of any of embodiment 80, wherein the metal component is Ni.

82. The process of any of embodiments 80-81, wherein the metal component is present at a metal loading in the range of from about 0.5 wt % to about 99 wt %.

83. The process of any of embodiments 80-82, wherein the contacting step is carried out at a temperature in the range of from about 80° C. to about 150° C.

84. The process of any of embodiments 80-83, wherein the hydrogen is present at a pressure in the range of from about 50 psig to about 2000 psig.

85. The process of any of embodiments 80-84, wherein the BHMTHF is produced at a selectivity of at least about 90%.

86. The process of any of embodiments 80-85, wherein at least about 85% of BHMF is converted to BHMTHF.

87. A process for producing a $C_3$-$C_6$ diol from a corresponding $C_3$-$C_6$ polyol, the process comprising:
contacting a $C_3$-$C_6$ polyol with hydrogen in the presence of a hydrodeoxygenation catalyst comprising a porous, shaped metal-carbon product to form a corresponding $C_3$-$C_6$ diol, wherein the metal component of the metal-carbon product is selected from the group consisting of Pd, Pt, Ir, Mo, W, V, Mn, Re, Zr, Ni, Cu, La, Sm, Y, Zn, Cr, Ge, Sn, Ti, Au, Rh, Co, and combinations thereof.

88. The process of any of embodiments 87, wherein the metal component is Ni.

89. The process of any of embodiments 87-88, wherein the metal component is present at a metal loading in the range of from about 0.5 wt % to about 10 wt %.

90. The process of any of embodiments 87-89, wherein the $C_3$-$C_6$ polyol is selected from the group consisting of 1,2,6-hexanetriol, 1,2,5-pentanetriol, 2H-tetrahydropyran-2-methanol, tetrahydrofuran-2,5-dimethanol, furan-2,5-dimethanol, 2,5-dihydrofuran-2,5-dimethanol, levoglucosenone, levoglucosan, levoglucosenol, 1,6-anhydro-3,4-dideoxy-p-D-pyranose-2-one, isosorbide, hydroxymethylfurfural, sorbitol, glucose, fructose, xylitol, 3,4-dihydro-2H-pyran-2-carbaldehyde, 1,2,5,6-hexanetetraol, 1,2,3,5,6-hexanepentanol, 1,5-anhydro-3,4-dideoxyhexitol, 5-hydroxy-2H-tetrahydropyran-2 methanol, furfural, furfuryl alcohol, tetrahydrofurfuryl alcohol, a pentose, and a hexose.

91. The process of any of embodiments 87-90, wherein the $C_3$-$C_6$ diol is selected from the group consisting of 1,5-pentanediol and 1,6-hexanediol.

92. The process of any of embodiments 87-91, wherein the porous shaped metal-carbon product further comprises Pt deposited on the surfaces of the porous shaped metal-carbon product.

93. The process of any of embodiments 87-92, wherein the $C_3$-$C_6$ polyol is 1,2,6-hexanetriol and the $C_3$-$C_6$ diol is 1,6-hexanediol.

94. The process of any of embodiments 87-93, wherein the contacting step is carried out at a temperature in the range of from about 80° C. to about 200° C.

95. The process of any of embodiments 87-94, wherein the hydrogen is present at a pressure in the range of from about 200 psig to about 3000 psig.

96. The process of any of embodiments 87-95, wherein the $C_3$-$C_6$ diol is produced at a selectivity of at least about 80%.

97. A process for producing 1,6-hexamethylenediamine (HMDA) from 1,6-hexanediol (HDO), the process comprising:
contacting 1,6-hexanediol with an amine in the presence of an amination catalyst comprising a porous, shaped metal-carbon product to form HMDA, wherein the metal component of the porous, shaped metal-carbon product is a metal selected from the group consisting of Ni, Ru, and Rh.

98. A process for producing glucaric acid from glucose, the process comprising:
contacting glucose with oxygen in the presence of an oxidation catalyst comprising a porous, shaped metal-carbon product to form glucaric acid, wherein the metal component of the porous, shaped metal-carbon product is a base metal.

99. The process of embodiment 98, wherein the porous, shaped metal-carbon product further comprises a noble metal deposited thereon.

100. A process for producing a dicarboxylic acid from an aldaric acid, or salt, ester, or lactone thereof, the process comprising:
contacting an aldaric acid, or salt, ester or lactone thereof with hydrogen in the presence of a halogen-containing compound and a hydroxygenation catalyst comprising a porous, shaped metal-carbon product of the present invention to form a dicarboxylic acid, wherein the metal component of the porous, shaped metal-carbon product is a base metal.

101. The process of embodiment 100, wherein the porous, shaped metal-carbon product further comprises a noble metal deposited thereon.

102. A process for producing 2,5-bis-hydroxymethylfuran (BHMF) from 5-hydroxymethylfurfural (HMF), the method comprising:
contacting HMF with hydrogen in the presence of a hydrogenation catalyst comprising a porous, shaped metal-carbon product of the present invention to form BHMF, wherein the metal component of the porous, shaped metal-carbon product is selected from the group consisting of Ni, Zn, Co, Cu, Ag, Pt, Pd, Fe, Ru, Au, W, Sb, Bi, Pb, and combinations thereof.

The foregoing and other aspects of the invention may be better understood in connection with the following non-limiting examples.

EXAMPLES

Example 1

Preparation of a 10% Ni-Carbon Catalyst 33.80 g Nickel carbonate, basic hydrate $NiCO_3.2Ni(OH)_2.xH_2O$ (Mw 358.12 x=3) from Sigma-Aldrich (SKU 544183) was added to an aqueous solution (250 g) containing 42.0 wt. % glucose (ADM Corn Processing, Dextrose Monohydrate 99.7DE with 91.2255 wt % Glucose content) and 3.0 wt. % hydroxyethylcellulose from Sigma-Aldrich (SKU 54290, viscosity 80-125 cP, 2% in $H_2O$ at 20° C.) to form a suspension with stirring. 100 g of carbon black powder (Timcal Ensaco 250 g, 65 m²/g) was then added to above suspension. The mixture was mixed in a laboratory muller, which was running for 2 hours to ensure good mixing and kneading of material. The material was then loaded into a 1" Bonnot BB Gun Extruder and extrudated into spaghetti like strings with ca. 1.5 mm diameter at cross section. These strings were dried under a dry air purge in a 120° C. oven overnight. Then they were treated at 800° C. for 2 hours with 30° C./min temperature ramp rate under continuous $N_2$ flow to produce carbon black extrudates. Finally catalysts has been reduced at 430 C for 6 hrs in the forming gas flow (5% $H_2$, 95% $N_2$) and passivated with the gas mixture 0.1% $O_2$ in $N_2$ for 2 hrs at room temperature.

Example 2

Preparation of a 15% Ni-Carbon Catalyst 54.65 g Nickel carbonate, basic hydrate $NiCO_3.2Ni(OH)_2 \cdot xH_2O$ (Mw 358.12 x=3) from Sigma-Aldrich (SKU 544183) was added to an aqueous solution (250 g) containing 42.0 wt. % glucose (ADM Corn Processing, Dextrose Monohydrate 99.7DE with 91.2255 wt % Glucose content) and 3.0 wt. % hydroxyethylcellulose from Sigma-Aldrich (SKU 54290, viscosity 80-125 cP, 2% in $H_2O$ at 20° C.) to form a suspension with stirring. 100 g of carbon black powder (Timcal Ensaco 250 g, 65 $m^2$/g) was then added to above suspension and the mixture was mixed in a laboratory muller, which was running for 2 hours to ensure good mixing and kneading of material. The material was then loaded into a 1" Bonnot BB Gun Extruder and extrudated into spaghetti like strings with ca. 1.5 mm diameter at cross section. These strings were dried under a dry air purge in a 120° C. oven overnight. Then they were treated at 800° C. for 2 hours with 30° C./min temperature ramp rate under continuous $N_2$ flow to produce carbon black extrudates. Finally catalysts has been reduced at 430 C for 6 hrs in the forming gas flow (5% $H_2$, 95% $N_2$) and passivated with the gas mixture 0.1% $O_2$ in $N_2$ for 2 hrs at room temperature.

Example 3

Preparation of 20% Ni-Carbon Catalyst 79.10 g Nickel carbonate, basic hydrate $NiCO_3.2Ni(OH)_2 \cdot xH_2O$ (Mw 358.12 x=3) from Sigma-Aldrich (SKU 544183) was added to an aqueous solution (250 g) containing 42.0 wt. % glucose (ADM Corn Processing, Dextrose Monohydrate 99.7DE with 91.2255 wt % Glucose content) and 3.0 wt. % hydroxyethylcellulose from Sigma-Aldrich (SKU 54290, viscosity 80-125 cP, 2% in $H_2O$ at 20° C.) to form a suspension with stirring. 100 g of carbon black powder (Timcal Ensaco 250G, 65 $m^2$/g) was then added to above suspension and the mixture was mixed in a laboratory muller, which was running for 2 hours to ensure good mixing and kneading of material. The material was then loaded into a 1" Bonnot BB Gun Extruder and extrudated into spaghetti like strings with ca. 1.5 mm diameter at cross section. These strings were dried under a dry air purge in a 120° C. oven overnight. Then they were treated at 800° C. for 2 hours with 30° C./min temperature ramp rate under continuous $N_2$ flow to produce carbon black extrudates. Finally catalysts has been reduced at 430 C for 6 hrs in the forming gas flow (5% $H_2$, 95% $N_2$) and passivated with the gas mixture 0.1% $O_2$ in $N_2$ for 2 hrs at room temperature.

Example 4

Preparation of Comparative Ni-Alumina Catalyst 25.6 g of $Ni(NO_3)_2 \times 6\ H_2O$ (Alfa-Aesar) was dissolved in 15 ml DI water. 6 ml of this solution was added to 6 g of Alumina carrier (XA 31132, Saint-Gobain). Material was dried at 120° C., 2 hrs and calcined at 350° C. for 3 h. Then the material was reduced in forming gas (5% $H_2$, 95% $N_2$) for 6 hrs at temperature 430° C. and passivated with the gas mixture 0.1% $O_2$ in $N_2$ for 2 hrs. Calculated Ni loading was 15.3 wt %.

Example 5

Catalytic Hydrogenation Activity Test

All catalysts including comparative example were tested in high throughput mode in a HiP-HOSS reactor (see "High-Throughput Heterogeneous Catalyst Research," Howard W. Turner, Anthony F. Volpe Jr, and W. H. Weinberg, *Surface Science* 603 (2009) 1763-1769, which is incorporated herein by reference) according to following procedure. 20 mg catalysts have been placed in 1 ml vials, filled with 0.2 ml of 0.4M solution of BHMF (2,5 dimethanol furan) in solvent 90% i-PA+10% $H_2O$ (v/v). The test was conducted at a temperature of 110° C. for 3 hrs under hydrogen pressure 700 psi. Observed products were 2,5 BHMTHF (2,5 dimethanol tetrahydrofuran) and 1,2,6 HTO (1,2,6-hexane triol). The results are provided in Table 1.

TABLE 1

Hydrogenation Activity

| Example No. | Catalyst | BHMTHF Yield, % | 1,2,6-HTO Yield, % | Mass Balance, % | BHMTHF selectivity, % (BHMTHF) |
|---|---|---|---|---|---|
| 1 | 10% Ni/C | 84 | 0 | 84 | 84 |
| 2 | 15% Ni/C | 97 | 0 | 97 | 97 |
| 3 | 20% Ni/C | 92 | 0 | 92 | 92 |
| 4 (comparative) | 15.3% Ni/$Al_2O_3$ | 91 | 7 | 99 | 92 |

The results indicate that Ni—C catalysts prepared according to this invention procedure possess good hydrogenation activity and selectivity for double bond hydrogenation that is comparable to performance of Ni on alumina catalysts with similar Ni loading.

Example 6

Preparation of Tungsten Containing Carbon Black Extrudates Using Carbon Black Powder and Carbohydrate Based Binders 200 g of carbon black powder (Timcal Ensaco 250G, 65 $m^2$/g) was added to an aqueous solution (500 g) containing 42.0 wt. % glucose (ADM Corn Processing, Dextrose Monohydrate 99.7DE with 91.2255 wt % Glucose content), 3.0 wt. % hydroxyethylcellulose from Sigma-Aldrich (SKU 54290, viscosity 80-125 cP, 2% in $H_2O$ at 20° C.), and 0.82 wt. % ammonium metatungstate hydrate from Sigma-Aldrich (SKU 358975). The mixture was mixed in a laboratory muller, which was running for 2 hours to ensure good mixing and kneading of material. The material was then loaded into a 1" Bonnot BB Gun Extruder and extrudated into spaghetti like strings with ca. 1.5 mm diameter at cross section. These strings were dried under a dry air purge in a 120° C. oven overnight. Then they were treated at 800° C. for 2 hours with 30° C./min temperature ramp rate under continuous $N_2$ flow to produce carbon black extrudates. By using other carbon black powders and carbohydrate binders with various amount of other tungsten containing species, different carbon black extrudates were prepared in a similar manner.

Example 7

Preparation of Platinum on Tungsten Containing Carbon Black Extrudates 15 g of tungsten containing carbon black extrudates from Example 6 was divided evenly into thirty 40 ml vials. A suitably concentrated aqueous solution of $Pt(NO_3)_2$ (Heraeus) (ca. 4.3 wt % Pt) was added to thirty vials and agitated to impregnate the support. The samples were dried in an oven at 60° C. for 3 hours under static air; then calcined at 360° C. under an air atmosphere for 2 hours with 5° C./min temperature ramp rate. Mass loss of ca. 10% was recorded during the thermo-treatment, leading to the final catalyst metal content being approximately 5.9 wt % Pt and 1.2 wt % W.

Example 8

Catalytic Hydrodeoxygenation Activity Test

Reaction was conducted in a ½" OD by 83 cm long 316 stainless steel tube with co-current down-flow of gas and liquid. Catalyst bed was vibration packed with 1.0 mm glass beads at the top to approximately 40 cm depth, followed by catalyst (28.5 cm bed depth containing 10.0 g), then SiC at the bottom to approximately 8 cm depth. Quartz wool plugs separated the catalyst bed from the SiC.

The packed reactor tube was clamped in an aluminum block heater equipped with PID controller at 120° C. Gas (hydrogen) and liquid flow of 0.4 M 1,2,6-hexanetriol (Spectrum Chemical and TCI America) in water was regulated by mass flow controller and HPLC pump, respectively. A back pressure regulator controlled reactor pressure at 1000 psig. The catalyst was tested for ca. 429 hours ToS under the above conditions. The liquid phase eluent was diluted with methanol and analyzed by gas chromatography with flame ionization detection. Table 2 describes the fixed bed reactor conditions and resulting catalyst performance.

TABLE 2

| | | 1,2,6-Hexanetriol to 1,6-Hexanediol | | | | |
|---|---|---|---|---|---|---|
| ToS (hours) | Flow (ml/min) | 1,2,6-HTO Remaining | 1,6-HDO Yield (% Sel) | 1,2-HDO Yield | 1,5-HDO Yield | 1-Hexanol Yield | 2-Hexanol Yield |
| 43 | 1 | 38% | 51% (82%) | 1% | 1% | 6% | <1% |
| 253 | 1 | 66% | 29% (87%) | <1% | 1% | 1% | <1% |
| 319 | 0.5 | 54% | 41% (88%) | <1% | 1% | 3% | <1% |
| 427 | 0.5 | 62% | 34% (89%) | <1% | 1% | 2% | <1% |

Example 9

Preparation of Tungsten Containing Carbon Black Extrudates Using Carbon Black Powder and Carbohydrate Based Binders 200 g of carbon black powder (Timcal Ensaco 250G, 65 $m^2/g$) was added to an aqueous solution containing 275 g water, 210 g glucose (ADM Corn Processing, Dextrose Monohydrate 99.7DE with 91.2255 wt % Glucose content), 15 g hydroxyethylcellulose from Sigma-Aldrich (SKU 54290, viscosity 80-125 cP, 2% in $H_2O$ (20° C.)), and (Support ID b) 8.35 g; (Support ID "c") 19.95 g; (Support ID "d") 33.65 g of ammonium metatungstate hydrate ("AMT") from Sigma-Aldrich (SKU 358975). The mixture was mixed in a laboratory muller, which was running for 2 hours to ensure good mixing and kneading of material. The material was then loaded into a 1" Bonnot BB Gun Extruder and extruded into spaghetti like strings with ca. 1.5 mm diameter at cross section. These strings were dried under a dry air purge in a 120° C. oven overnight. Then they were treated at 800° C. for 2 hours with 30° C./min temperature ramp rate under continuous $N_2$ flow to produce carbon black extrudates.

Varying amounts of Tungsten (VI) oxide from Strem Chemicals (Lot 25575500): (Support ID "e") 0.92 g; (Support ID "f") 1.86 g; (Support ID "g") 3.76 g and 100 g of carbon black powder (Timcal Ensaco 250G, 65 $m^2/g$) were added to an aqueous solution containing 135 g water, 105 g glucose (ADM Corn Processing, Dextrose Monohydrate 99.7DE with 91.2255 wt % Glucose content), 7.5 g hydroxyethylcellulose from Sigma-Aldrich (SKU 54290, viscosity 80-125 cP, 2% in $H_2O$ (20° C.)). The mixture was mixed in a laboratory muller, which was running for 2 hours to ensure good mixing and kneading of material. The material was then loaded into a 1" Bonnot BB Gun Extruder and extruded into spaghetti like strings with ca. 1.5 mm diameter at cross section. These strings were dried under a dry air purge in a 120° C. oven overnight. Then they were treated at 800° C. for 2 hours with 30° C./min temperature ramp rate under continuous $N_2$ flow to produce carbon black extrudates.

Example 10

Preparation of Platinum on Tungsten Containing Carbon Black Extrudates (Support ID b in Table 3)

15 g of tungsten containing carbon black extrudates (2 wt % W) from Example 9 was divided evenly into thirty 40 ml vials. A suitably concentrated aqueous solution of $Pt(NO_3)_2$ (Heraeus) was added to thirty vials and agitated to impregnate the support. The samples were dried in an oven at 60° C. for 3 hours under static air; then calcined at 360° C. under an air atmosphere for 2 hours with 5° C./min temperature ramp rate. The contents of the thirty vials were combined. Mass loss of ca. 5% was recorded during the thermo-treatment, leading to the final catalyst metal content being approximately 5.1 wt % Pt and 2 wt % W. One 0.25 g sample of the final catalyst was further thermally treated at 75° C. under a 5% hydrogen/95% nitrogen atmosphere for 3 hours with 5° C./min temperature ramp rate.

Example 11

Preparation of Platinum on Tungsten Containing Carbon Black Extrudates (Support ID c-g in Table 3)

0.5 g of each of the tungsten containing carbon black extrudates from Example 10 was divided evenly into one of five 40 ml vials. A suitably concentrated aqueous solution of $Pt(NO_3)_2$ (Heraeus) was added to each vial and agitated to impregnate the support. The samples were dried in an oven at 60° C. for 3 hours under static air; then calcined at 360° C. under an air atmosphere for 2 hours with 5° C./min temperature ramp rate. 0.25 g sample of each of the above catalysts was further thermally treated at 75° C. under a 5% hydrogen/95% nitrogen atmosphere for 3 hours with 5° C./min temperature ramp rate.

Example 12

Testing of Platinum on Tungsten Containing Carbon Black Extrudates in a Batch Reactor for the Hydrodeoxygenation of 1,2,6-Hexanetriol to 1,6-Hexanediol These twelve extrudate catalysts were tested for 1,2,6-hexanetriol (Spectrum Chemical) reduction using the following catalyst testing protocol. The extrudate catalysts were crushed. A small sample of each catalyst (ca. 10 mg) was weighed into glass vial inserts, followed by addition of an aqueous 1,2,6-hexanetriol solution (200 μl of 0.8 M). The glass vial inserts were loaded into a reactor and the reactor was closed. The atmosphere in the reactor was replaced with hydrogen and pressurized to 670 psig at room temperature. The reactor was heated to 160° C. and maintained at 160° C. for 2.5 hours while vials were shaken. After 2.5 hours, shaking was stopped and reactor was cooled to 40° C. Pressure in the reactor was then slowly released. The glass vial inserts were removed from the reactor. The solutions were diluted with methanol and analyzed by gas chromatography with flame ionization detection. The results are summarized in Table 3.

TABLE 3

1,2,6-Hexanetriol to 1,6-Hexanediol

| Support ID | wt % W | W Source | Thermo-treatment | 1,6-HDO Yield (% Selectivity) |
|---|---|---|---|---|
| b | 2.0 | AMT | C: 360° C., 2 hrs | 32% (87%) |
| c | 4.6 | AMT | C: 360° C., 2 hrs | 18% (82%) |
| d | 7.5 | AMT | C: 360° C., 2 hrs | 21% (84%) |
| e | 0.5 | $WO_3$ | C: 360° C., 2 hrs | 3% (64%) |
| f | 1.0 | $WO_3$ | C: 360° C., 2 hrs | 11% (71%) |
| g | 2.0 | $WO_3$ | C: 360° C., 2 hrs | 9% (77%) |
| b | 2.0 | AMT | C: 360° C., 2 h + R: 75° C., 3 hrs | 38% (89%) |
| c | 4.6 | AMT | C: 360° C., 2 h + R: 75° C., 3 hrs | 23% (84%) |
| d | 7.5 | AMT | C: 360° C., 2 h + R: 75° C., 3 hrs | 17% (81%) |
| e | 0.5 | $WO_3$ | C: 360° C., 2 h + R: 75° C., 3 hrs | 4% (66%) |
| f | 1.0 | $WO_3$ | C: 360° C., 2 h + R: 75° C., 3 hrs | 9% (76%) |
| g | 2.0 | $WO_3$ | C: 360° C., 2 h + R: 75° C., 3 hrs | 14% (76%) |

C—calcination conditions
R—reduction conditions

Example 13

Preparation of Gold—Platinum on Tungsten Containing Crushed Carbon Black Extrudates 0.1 g of each of the tungsten containing carbon black extrudates from Example 9 was placed in a 4 ml vials and crushed to powder. A suitably concentrated aqueous solution of NMe4AuO2 and PtO(NO3) was added to the six vials and agitated to impregnate the support. The samples were dried in an oven at 60° C. for 3 hours under 5% hydrogen/95% nitrogen atmosphere; followed by further treatment at 350° C. for 3 hours with 5° C./min temperature ramp rate. Each catalysts' metal loading was ca. 0.51 wt % Au; 0.93 wt % Pt.

Example 14

Testing of Gold—Platinum on Tungsten Containing Crushed Carbon Black Extrudates in a Batch Reactor for the Oxidation of Glucose to Glucaric Acid Six catalysts were tested for glucose (ADM) oxidation using the following catalyst testing protocol. Catalyst (ca. 16 mg) were weighed into glass vial inserts followed by addition of an aqueous glucose solution (250 μl of 20 wt. %). The glass vial inserts were loaded into a reactor and the reactor was closed. The atmosphere in the reactor was replaced with oxygen and pressurized to 150 psig at room temperature. Reactor was heated to 110° C. and maintained at 110° C. for 2 hours while vials were shaken. After 2 hours, shaking was stopped and reactor was cooled to 40° C. Pressure in the reactor was then slowly released. The glass vial inserts were removed from the reactor. The solutions were diluted with water and analyzed by ion chromatography with CAD/connectivity detection. A summary of the results is provided in Table 4.

TABLE 4

Glucose to Glucaric Acid Yield

| Support ID | wt % W | W Source | Glucose Conversion | Glucaric Acid Yield |
|---|---|---|---|---|
| b* | 2.0 | AMT | 88% | 15% |
| c | 4.6 | AMT | 81% | 12% |
| d | 7.5 | AMT | 88% | 19% |
| e | 0.5 | $WO_3$ | 82% | 13% |
| f | 1.0 | $WO_3$ | 90% | 17% |
| g | 2.0 | $WO_3$ | 94% | 21% |

*12 mg of catalyst used

While preferred embodiments of the invention have been illustrated and described, it will be appreciated that various changes can be made therein without departing from the spirit and scope of the invention.

We claim:

1. A process for producing a $C_3$-$C_6$ diol from a corresponding $C_3$-$C_6$ polyol, the process comprising:
    contacting the $C_3$-$C_6$ polyol with hydrogen in the presence of a hydrodeoxygenation catalyst comprising a porous, shaped metal-carbon product to form the corresponding $C_3$-$C_6$ diol, wherein the metal-carbon product comprises at least one metal component selected from the group consisting of Pd, Pt, Ir, Mo, W, V, Mn, Re, Zr, Ni, Cu, La, Sm, Y, Zn, Cr, Ge, Sn, Ti, Au, Rh, Co, and combinations thereof.

2. The process of claim 1, wherein the metal component comprises Mo, W, or a mixture thereof.

3. The process of claim 1, wherein the metal component is present at a metal loading in the range of from about 0.5 wt % to about 10 wt %.

4. The process of claim 1, wherein the $C_3$-$C_6$ polyol is selected from the group consisting of 1,2,6-hexanetriol, 1,2,5-pentanetriol, 2H-tetrahydropyran-2-methanol, tetrahydrofuran-2,5-dimethanol, furan-2,5-dimethanol, 2,5-dihydrofuran-2,5-dimethanol, levoglucosenone, levoglucosan, levoglucosenol, 1,6-anhydro-3,4-dideoxy-p-D-pyranose-2-one, isosorbide, hydroxymethylfurfural, sorbitol, glucose, fructose, xylitol, 3,4-dihydro-2H-pyran-2-carbaldehyde, 1,2,5,6-hexanetetraol, 1,2,3,5,6-hexanepentanol, 1,5-anhydro-3,4-dideoxyhexitol, 5-hydroxy-2H-tetrahydropyran-2 methanol, furfural, furfuryl alcohol, tetrahydrofurfuryl alcohol, a pentose, and a hexose.

5. The process of claim 1, wherein the $C_3$-$C_6$ diol is selected from the group consisting of 1,5-pentanediol and 1,6-hexanediol.

6. The process of claim 1, wherein the $C_3$-$C_6$ polyol comprises 1,2,6-hexanetriol and the $C_3$-$C_6$ diol comprises 1,6-hexanediol.

7. The process of claim 1, wherein the porous, shaped metal-carbon product further comprises a metal deposited on the surfaces of the porous, shaped metal-carbon product.

8. The process of claim 1, wherein the porous, shaped metal-carbon product further comprises Pt deposited on the surfaces of the porous, shaped metal-carbon product.

9. The process of claim 8, wherein the metal component of the porous, shaped metal-carbon product comprises W.

10. The process of claim 1, wherein the contacting step is carried out at a temperature in the range of from about 80° C. to about 200° C.

11. The process of claim 1, wherein the hydrogen is present at a pressure in the range of from about 200 psig to about 3000 psig.

12. The process of claim 1, wherein the $C_3$-$C_6$ diol is produced at a selectivity of at least about 80%.

13. The process of claim 1, wherein the porous, shaped metal-carbon product exhibits a radial piece crush strength of greater than about 4.4 N/mm (1 lb/mm).

14. The process of claim 1, wherein no more than about 10% of the pore volume of the porous, shaped metal-carbon product is from pores having a pore diameter less than about 10 nm.

15. The process of claim 1, wherein the porous, shaped metal-carbon product comprises a specific pore volume of pores having a diameter in the range of from 1.7 nm to 100 nm, as measured by the BJH process, that is from about 0.1 $cm^3$/g to about 1.5 $cm^3$/g.

16. The process of claim 1, wherein the carbonaceous material comprises carbon black, activated carbon, and/or graphite.

17. The process of claim 1, wherein the carbonaceous material has a BET specific surface area of at least about 20 $m^2$/g.

18. The process of claim 1, wherein the carbonaceous material has a BET specific surface area in the range of from about 20 $m^2$/g to about 500 $m^2$/g.

19. The process of claim 1, wherein the porous, shaped metal-carbon product is a carbonized product of a carbonaceous material with water, a water-soluble organic binder, and a metal precursor of the metal component selected from the group consisting of a metal carbonate, a metal oxide, a metal hydroxide, a salt of a metal acid, a heteropoly acid, a metal carboxylate, a metal carbide, a metal chloride, a metal amine complex-containing compound, a hydrate thereof, and a mixture of any two or more thereof.

20. The process of claim 19, wherein the water-soluble binder comprises a cellulose and/or a sugar.

* * * * *